United States Patent
Amit et al.

(10) Patent No.: US 10,066,205 B2
(45) Date of Patent: *Sep. 4, 2018

(54) MEDIUM COMPRISING TRANSFORMING GROWTH FACTOR BETA 1 AND BASIC FIBROBLAST GROWTH FACTOR

(71) Applicant: Technion Research & Development Foundation Limited, Haifa (IL)

(72) Inventors: Michal Amit, Misgav (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,537

(22) Filed: Jul. 4, 2016

(65) Prior Publication Data

US 2016/0312180 A1 Oct. 27, 2016

Related U.S. Application Data

(60) Continuation of application No. 14/578,443, filed on Dec. 21, 2014, now Pat. No. 9,410,121, which is a continuation of application No. 14/058,347, filed on Oct. 21, 2013, now Pat. No. 8,945,925, which is a continuation of application No. 13/466,161, filed on May 8, 2012, now Pat. No. 8,563,311, which is a continuation of application No. 13/083,630, filed on Apr. 11, 2011, now Pat. No. 8,222,034, which is a division of application No. 12/585,646, filed on Sep. 21, 2009, now Pat. No. 7,955,851, which is a continuation of application No. 10/537,784, filed as application No. PCT/IL03/01030 on Dec. 7, 2003, now Pat. No. 7,592,175.

(60) Provisional application No. 60/433,619, filed on Dec. 16, 2002.

(51) Int. Cl.
| | |
|---|---|
| *C12N 5/0735* | (2010.01) |
| *C12N 5/074* | (2010.01) |
| *C12N 5/0789* | (2010.01) |
| *C12N 5/00* | (2006.01) |
| *C12N 5/0797* | (2010.01) |

(52) U.S. Cl.
CPC ......... *C12N 5/0606* (2013.01); *C12N 5/0607* (2013.01); *C12N 5/0611* (2013.01); *C12N 5/0647* (2013.01); *C12N 5/0031* (2013.01); *C12N 5/0037* (2013.01); *C12N 5/0043* (2013.01); *C12N 5/0056* (2013.01); *C12N 5/0623* (2013.01); *C12N 5/0696* (2013.01); *C12N 2500/25* (2013.01); *C12N 2500/84* (2013.01); *C12N 2500/90* (2013.01); *C12N 2500/98* (2013.01); *C12N 2501/10* (2013.01); *C12N 2501/115* (2013.01); *C12N 2501/119* (2013.01); *C12N 2501/125* (2013.01); *C12N 2501/15* (2013.01); *C12N 2501/155* (2013.01); *C12N 2501/235* (2013.01); *C12N 2501/33* (2013.01); *C12N 2501/998* (2013.01); *C12N 2533/52* (2013.01)

(58) Field of Classification Search
CPC .. C12N 5/0606; C12N 5/0607; C12N 5/0611; C12N 5/0647; C12N 5/0031; C12N 5/0037; C12N 5/0043; C12N 5/0056; C12N 5/0623; C12N 5/0696; C12N 2500/25; C12N 2500/84; C12N 2500/90; C12N 2500/98; C12N 2501/10; C12N 2501/115; C12N 2501/119; C12N 2501/125; C12N 2501/15; C12N 2501/155; C12N 2501/235; C12N 2501/33; C12N 2501/998; C12N 2533/52
See application file for complete search history.

(56) References Cited

U.S. PATENT DOCUMENTS

| | | | |
|---|---|---|---|
| 5,612,211 A | 3/1997 | Wilson et al. | |
| 6,103,529 A * | 8/2000 | Price ................... | C12N 5/0043 435/325 |
| 6,245,566 B1 | 6/2001 | Gearhart et al. | |
| 6,576,464 B2 | 6/2003 | Gold et al. | |
| 6,642,048 B2 | 11/2003 | Xu et al. | |
| 7,250,294 B2 | 7/2007 | Carpenter et al. | |
| 7,297,539 B2 | 11/2007 | Mandalam et al. | |
| 7,413,902 B2 | 8/2008 | Bodnar et al. | |
| 7,413,904 B2 | 8/2008 | Gold et al. | |
| 7,432,104 B2 | 10/2008 | Mitalipova et al. | |
| 7,452,718 B2 | 11/2008 | Gold et al. | |
| 7,455,983 B2 | 11/2008 | Xu et al. | |

(Continued)

FOREIGN PATENT DOCUMENTS

| | | |
|---|---|---|
| AU | 2004294835 | 6/2005 |
| AU | 2009213101 | 10/2009 |
| CA | 2388811 | 7/2001 |
| CA | 2468335 | 6/2003 |
| CA | 2470539 | 6/2003 |

(Continued)

OTHER PUBLICATIONS

Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*

(Continued)

*Primary Examiner* — Thaian N Ton

(57) ABSTRACT

The present invention is of methods of establishing and propagating human embryonic stem cell lines using feeder cells-free, xeno-free culture systems and stem cells which are capable of being maintained in an undifferentiated, pluripotent and proliferative state in culture which is free of xeno contaminants and feeder cells.

14 Claims, 11 Drawing Sheets
(8 of 11 Drawing Sheet(s) Filed in Color)

Specification includes a Sequence Listing.

(56) References Cited

U.S. PATENT DOCUMENTS

| | | | |
|---|---|---|---|
| 7,473,555 B2 | 1/2009 | Mandalam et al. | |
| 7,504,257 B2 | 3/2009 | Reubinoff et al. | |
| 7,560,281 B2 | 7/2009 | Carpenter et al. | |
| 7,592,175 B2 | 9/2009 | Amit et al. | |
| 7,638,328 B2 | 12/2009 | Eriksson et al. | |
| 7,641,897 B2 | 1/2010 | Weissman et al. | |
| 7,851,167 B2 | 12/2010 | Xu | |
| 7,892,835 B2 | 2/2011 | Akaike et al. | |
| 7,897,389 B2 | 3/2011 | Gold et al. | |
| 7,955,851 B2 | 6/2011 | Amit et al. | |
| 8,067,233 B2 | 11/2011 | Totey et al. | |
| 8,222,034 B2 | 7/2012 | Amit et al. | |
| 8,252,585 B2 | 8/2012 | Carpenter | |
| 8,252,586 B2 | 8/2012 | Carpenter et al. | |
| 8,318,486 B2 | 11/2012 | Amit et al. | |
| 8,563,311 B2 | 10/2013 | Amit et al. | |
| 8,597,947 B2 | 12/2013 | Reubinoff | |
| 8,637,311 B2 | 1/2014 | Mandalam et al. | |
| 8,945,925 B2 | 2/2015 | Amit et al. | |
| 9,410,121 B2 * | 8/2016 | Amit ................... | C12N 5/0606 |
| 2002/0127715 A1 | 9/2002 | Benvenisty et al. | |
| 2002/0168763 A1 | 11/2002 | Yan et al. | |
| 2003/0153082 A1 | 8/2003 | Bhatia | |
| 2003/0211603 A1 | 11/2003 | Earp et al. | |
| 2003/0224411 A1 | 12/2003 | Stanton et al. | |
| 2004/0009593 A1 | 1/2004 | Keirstead et al. | |
| 2004/0014211 A1 | 1/2004 | Ogle et al. | |
| 2004/0067580 A1 | 4/2004 | Amit et al. | |
| 2004/0110286 A1 | 6/2004 | Bhatia | |
| 2004/0180347 A1 | 9/2004 | Stanton et al. | |
| 2004/0191901 A1 | 9/2004 | Assady et al. | |
| 2005/0032207 A1 | 2/2005 | Wobus et al. | |
| 2005/0038146 A1 | 2/2005 | Fish et al. | |
| 2005/0054093 A1 | 3/2005 | Haas | |
| 2005/0095703 A1 | 5/2005 | Semb et al. | |
| 2005/0101014 A1 | 5/2005 | Keirstead et al. | |
| 2005/0153444 A1 | 7/2005 | Mandalam et al. | |
| 2005/0153445 A1 | 7/2005 | Mandalam et al. | |
| 2005/0210537 A1 | 9/2005 | Dominko et al. | |
| 2005/0214938 A1 | 9/2005 | Gold et al. | |
| 2005/0227352 A1 | 10/2005 | Xie | |
| 2005/0227353 A1 | 10/2005 | Mummery | |
| 2006/0051862 A1 | 3/2006 | Amit et al. | |
| 2006/0057720 A1 | 3/2006 | Xu et al. | |
| 2006/0134636 A1 | 6/2006 | Stanton et al. | |
| 2006/0252150 A1 | 11/2006 | Cheng | |
| 2007/0231898 A1 | 10/2007 | Keirstead et al. | |
| 2007/0280989 A1 | 12/2007 | Shahar et al. | |
| 2007/0298453 A1 | 12/2007 | Murdoch et al. | |
| 2008/0076176 A1 | 3/2008 | Dominko et al. | |
| 2008/0193421 A1 | 8/2008 | Kruse et al. | |
| 2008/0241919 A1 | 10/2008 | Parsons et al. | |
| 2009/0104695 A1 | 4/2009 | Shushan et al. | |
| 2009/0136559 A1 | 5/2009 | Athanasiou et al. | |
| 2009/0155218 A1 | 6/2009 | Hayek et al. | |
| 2010/0021999 A1 | 1/2010 | Amit et al. | |
| 2011/0189767 A1 | 8/2011 | Amit et al. | |
| 2012/0214232 A1 | 8/2012 | Amit et al. | |
| 2012/0322146 A1 | 12/2012 | Carpenter et al. | |
| 2013/0084563 A1 | 4/2013 | Amit et al. | |
| 2013/0130375 A1 | 5/2013 | Rudy-Reil | |
| 2014/0045266 A1 | 2/2014 | Amit et al. | |
| 2015/0104871 A1 | 4/2015 | Amit et al. | |

FOREIGN PATENT DOCUMENTS

| | | | |
|---|---|---|---|
| EP | 1809739 | 7/2007 | |
| JP | 2001-017163 | 1/2001 | |
| WO | WO 97/33995 | 9/1997 | |
| WO | WO 9804680 A1 * | 2/1998 | ........... C12N 5/0037 |
| WO | WO 98/30679 | 7/1998 | |
| WO | WO 99/20740 | 4/1999 | |
| WO | WO 99/20741 | 4/1999 | |
| WO | WO 00/17321 | 3/2000 | |
| WO | WO 01/21766 | 3/2001 | |
| WO | WO 01/51616 | 7/2001 | |
| WO | WO 01/88104 | 11/2001 | |
| WO | WO 02/31123 | 4/2002 | |
| WO | WO 03/029443 | 4/2003 | |
| WO | WO 03100026 A2 * | 12/2003 | ........... C12N 5/0676 |
| WO | WO 2004/055155 | 7/2004 | |
| WO | WO 2006/020889 | 2/2006 | |

OTHER PUBLICATIONS

Jean et al. Develop. Growth Differ., (55): 41-51, 2013.*
Sato et al. (2004) Nat. Med. 10:55-63.*
Humphrey et al. (2004) Stem Cells 22: 522-530.*
Li et al., Blood, 98: 335-342, 2001.*
Pucéat, Methods, 45: 168-171, 2008.*
Wobus et al. (1988) Biomed. Biochim Acta 12:965.*
Schuldiner (2000) PNAS 97:11307.*
Kramer et al. (2000) Mech. of Dev. 92:193.*
Johansson et al. (1995) Mol and Cell Biol. 15:141.*
Yu, "Embryonic Stem cells" 2006, accessed at https://stemcells.nih.gov/info/Regenerative_Medicine/2006Chapter1.htm, on Aug. 25, 2017, pp. 1-10.*
Requisition by the Examiner dated Aug. 19, 2016 From the Canadian Intellectual Property Office Re. Application No. 2,508,880.
Communication Pursuant to Rules 109 and 110 EPC dated Jul. 27, 2005 From the European Patent Office Re. Application No. 03813286.6.
Office Action dated Dec. 14, 2008 From the Israeli Patent Office Re. Application No. 168984.
Office Action dated Mar. 30, 2007 From the Patent Office of the People's Republic of China Re. Application No. 200380109688.7.
Communication Pursuant to Article 94(3) EPC dated Sep. 1, 2015 From the European Patent Office Re. Application No. 11190776.2.
Communication Pursuant to Article 94(3) EPC dated Nov. 15, 2010 From the European Patent Office Re. Application No. 03813286.6.
Communication Pursuant to Article 94(3) EPC dated Jul. 17, 2014 From the European Patent Office Re. Application No. 03813286.6.
Communication Pursuant to Article 94(3) EPC dated Mar. 18, 2013 From the European Patent Office Re. Application No. 03813286.6.
Communication Pursuant to Article 94(3) EPC dated Nov. 27, 2009 From the European Patent Office Re. Application No. 03813286.6.
Communication Pursuant to Article 94(3) EPC dated Jul. 28, 2014 From the European Patent Office Re. Application No. 11190776.2.
European Search Report and the European Search Opinion dated Mar. 20, 2013 From the European Patent Office Re. Application No. 11190776.2.
Examiner's Report dated May 4, 2011 From the Australia Government, IP Australia Re. Application No. 2009202968.
Examiner's Report dated Jan. 10, 2012 From the Australia Government, IP Australia Re. Application No. 2009202968.
Examiner's Report dated May 12, 2008 From the Australia Government, IP Australia Re. Application No. 2003303071.
International Preliminary Examination Report dated Jan. 25, 2006 From the International Preliminary Examining Authority Re. Application No. PCT/IL03/01030.
International Search Report dated Jul. 28, 2004 From the International Searching Authority Re. Application No. PCT/IL03/01030.
Office Action dated Mar. 5, 2012 From the Israel Patent Office Re. Application No. 207268 and Its Translation Into English.
Office Action dated Jan. 9, 2009 From the State Intellectual Property Office of the People's Republic of China Re. Application No. 200380109688.7.
Office Action dated Dec. 10, 2012 From the Israel Patent Office Re. Application No. 207268 and Its Translation Into English.
Office Action dated Dec. 14, 2008 From the Israeli Patent Office Re. Application No. 168984 and Its Translation Into English.
Official Action dated Dec. 3, 2013 From the US Patent and Trademark Office Re. U.S. Appl. No. 14/058,347.
Official Action dated Oct. 5, 2015 From the US Patent and Trademark Office Re. U.S. Appl. No. 14/578,443.
Official Action dated Dec. 6, 2012 From the US Patent and Trademark Office Re. U.S. Appl. No. 13/466,161.

(56) References Cited

OTHER PUBLICATIONS

Official Action dated Jul. 8, 2010 From the US Patent and Trademark Office Re. U.S. Appl. No. 12/585,646.
Official Action dated Oct. 9, 2007 From the US Patent and Trademark Office Re. U.S. Appl. No. 10/537,784.
Official Action dated Nov. 15, 2010 From the US Patent and Trademark Office Re. U.S. Appl. No. 12/585,646.
Official Action dated Sep. 15, 2008 From the US Patent and Trademark Office Re. U.S. Appl. No. 10/537,784.
Official Action dated Jun. 17, 2011 From the US Patent and Trademark Office Re. U.S. Appl. No. 13/083,630.
Official Action dated Jun. 24, 2014 From the US Patent and Trademark Office Re. U.S. Appl. No. 14/058,347.
Official Action dated Jun. 25, 2012 From the US Patent and Trademark Office Re. U.S. Appl. No. 13/466,161.
Official Action dated Jan. 28, 2008 From the US Patent and Trademark Office Re. U.S. Appl. No. 10/537,784.
Requisition by the Examiner dated Sep. 14, 2015 From the Canadian Intellectual Property Office Re. Application No. 2,508,880.
Requisition by the Examiner dated Jul. 24, 2013 From the Canadian Intellectual Property Office Re. Application No. 2,508,880.
Requisition by the Examiner dated Feb. 25, 2010 From the Canadian Intellectual Property Office Re. Application No. 2,508,880.
Requisition by the Examiner dated Aug. 26, 2011 From the Canadian Intellectual Property Office Re. Application No. 2,508,880.
Requisition by the Examiner dated Aug. 27, 2014 From the Canadian Intellectual Property Office Re. Application No. 2,508,880.
Requisition by the Examiner dated Aug. 31, 2012 From the Canadian Intellectual Property Office Re. Application No. 2,508,880.
Supplementary European Search Report dated Jan. 26, 2007 From the European Patent Office Re. Application No. 03813286.6.
Translation of Notice of Reason for Rejection dated Oct. 2, 2009 From the Japanese Patent Office Re. Application No. 2004-560155.
Translation of Notice of the Reason for Rejection dated Jan. 27, 2011 From the Korean Intellectual Property Office Re. Application No. 2005-7011099.
Translation of Notice of the Reason for Rejection dated Dec. 28, 2011 From the Korean Intellectual Property Office Re. Application No. 2005-7011099.
Translation of Official Decision of Rejection dated Apr. 2, 2010 From the Japanese Patent Office Re. Application No. 2004-560155.
Written Opinion dated Nov. 25, 2005 From the International Preliminary Examining Authority Re. Application No. PCT/IL03/01030.
Amit et al. "Clonially Derived Human Embryonic Stem Cell Lines Maintain Pluripotency and Proliferative Potential for Prolonged Periods of Culture", Developmental Biology, 227: 271-278, 2000.
Amit et al. "Feeder-Layer- and Serum-Free Culture of Human Embryonic Stem Cells", Biology of Reproduction, XP002978624, 70: 837-845, Jan. 2004.
Amit et al. "Human Feeder Layers for Human Embryonic Stem Cells", Biology of Reproduction, 68: 2150-2156, 2003.
Bell et al. "People: James Thomson—A Transplant Medicine Revolutionary", Bell & Howell Information and Learning, The Business Journal, 17(31): 43, Jun. 7, 2000.
Chen et al. "Chemically Defined Conditions for Human iPSC Derivation and Culture", Nature Methods, 8(5): 424-429 ff., May 2011.
Chen et al. "Chemically Defined Conditions for Human iPSC Derivation and Culture. Supplement", Nature Methods, p. 1-11, May 2011.
Gepstein "Derivation and Potential Applications of Human Embryonic Stem Cells", Circulation Research, 91(10): 866-876, Nov. 15, 2002.
Goldsborough et al. "Serum-Free Culture of Murine Embryonic Stem (ES) Cells", Focus, 20(1): 9-12, 1998.
Lebkowski et al. "Human Ebryonic Stem Cells: Culture, Differentiation, and Genetic Modifications for Regenerative Medicine Applications", The Cancer Journal, 7: S83-S93, 2001.
Li et al. "Leukemia Inhibitory Factor-Expressing Human Embryonic Lung Fibroblasts as Feeder Cells for Human Embryonic Germ Cells", Cells Tissues Organs, 186: 221-228, 2007.
Ludwig et al. "Derivation of Human Embryonic Stem Cells in Defined Conditions", Nature Biotechnology, Advanced Online Publication, p. 1-3, Jan. 1, 2006.
Ludwig et al. "Derivation of Human Embryonic Stem Cells in Defined Conditions. Supplemental Table 1. Complete Formulation for TeSR1 Medium", Nature Biotechnology, 1 P., Jan. 1, 2006.
Ludwig et al. "Feeder-Independent Culture of Human Embryonic Stem Cells", Nature Methods, 3(8): 637-646, Aug. 2006.
Mulder et al. "Characterization of a Serum-Free Culture System Comparing Growth Factor Requirements of Transformed and Untransformed Cells", Experimental Cell Research, 188: 254-261, 1990.
Murdoch et al. "Human Embryonic Derived Hematopoietic Repopulating Cells Require Distinct Factors to Sustain In Vivo Repoplating Function", Experimental Hematology, 30: 598-605, 2002.
Nakazawa et al. "Keratan Sulfate Synthesis by Corneal Stromal Cells Within Three-Dimensional Collagen Gel Cultures", The Journal of Biochemistry, 120(1): 117-125, 1996.
NIH "NIH and ES Cell International Pte. Ltd Sign International Stem Cell Research Agreement", National Institutes of Health (NIH) Communications, Public Release, Apr. 11, 2002.
Pei et al. "Serum Free Culture of Rhesus Monkey Embryonic Stem Cells", Archives of Andrology, 49: 331-342, 2003.
Richards et al. "Human Feeders Support Prolonged Undifferentiated Growth of Human Inner Cell Masses and Embryonic Stem Cells", Nature Biotechnology, Technical Report, XP002335247, 20: 933-936, Sep. 2002.
Rizzino "Behavior of Transforming Growth Factors in Serum-Free Media: An Improved Assay for Transforming Growth Factors", In Vitro, 20(10): 815-822, Oct. 1984.
Robertson "NIH Sacrifies Commercial Rights in WiCell Deal", Nature Biotechnology, 19(11): 1001, Nov. 2001.
Schuldiner et al. "Effects of Eight Growth Factors on the Differentiation of Cells Derived From Human Embryonic Stem Cells", Proc. Natl. Acad. Sci. USA, 97(21): 11307-11312, 2000.
Sigma "Tissue Culture Media and Reagents. Attachment and Matrix Factors", Biochemical Organic Compounds. Diagnostic Reagents, The Sigma Catalog, p. 1389, 1992.
Stojkovic et al. "Derivation, Growth and Applications of Human Embryonic Stem Cells", Reproduction, 128: 259-267, 2004.
Thomson et al. "Embryonic Stem Cell Lines Derived From Human Balstocysts", Science, 282: 1145-1147, 1998.
Verfaillie "Adult Stem Cells: Assessing the Case for Pluripotency", Trends in Cell Biology, 12(11): 502-508, Nov. 2002.
Weerda et al. "Effects of Transforming Growth Factor-Beta1 and Basic Fibroblast Growth Factor on Proliferation of Cell Cultures Derived From Human Vestibular Nerve Schwannoma", Acta Oto-Laryngologica, 118: 337-343, 1998.
Xu et al. "Feeder-Free Growth of Undifferentiated Human Embryonic Stem Cells", Nature Biotechnology, XP002282070, 19(10): 971-974, Oct. 2001.
Yamanishi et al. "Roles of Transforming Growth Factor Beta in Inhibition of Androgen-Induced Growth of Shionogi Carcinoma Cells in Serum-Free Medium", Cancer Research, 50: 6179-6183, Oct. 1, 1990.
Zhang "Feeder Layer- and Serum-Free Culture of Rhesus Monkey Embryonic Stem Cells", Reproductive BioMedicine Online, 13(3): 412-420, Jan. 1, 2006.
Zhang et al. "Mitogenic and Anti-Proliferative Signals for Neural Crest Cells and the Neurogenic Action of TGF-Beta1", Developmental Dynamics, 208: 375-386, 1997.
Communication Pursuant to Article 94(3) EPC dated Jun. 23, 2017 From the European Patent Office Re. Application No. 11190776.2. (4 Pages).

* cited by examiner

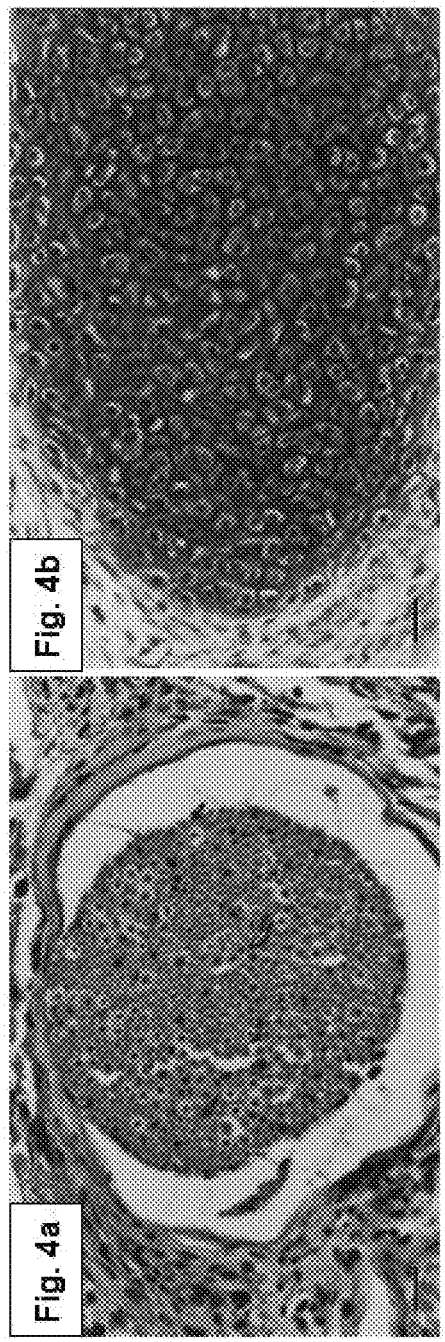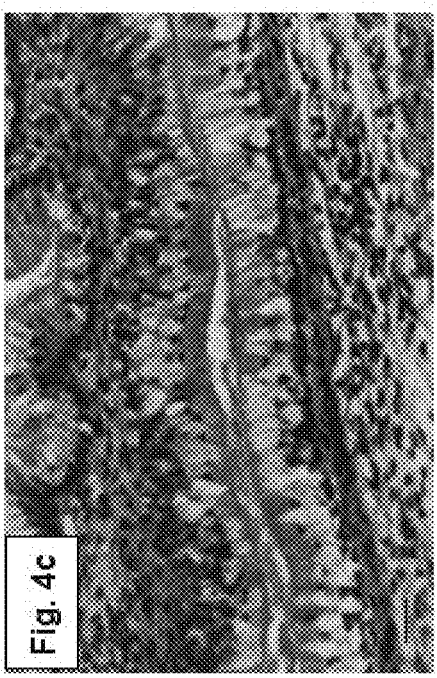
Figs. 4a-c

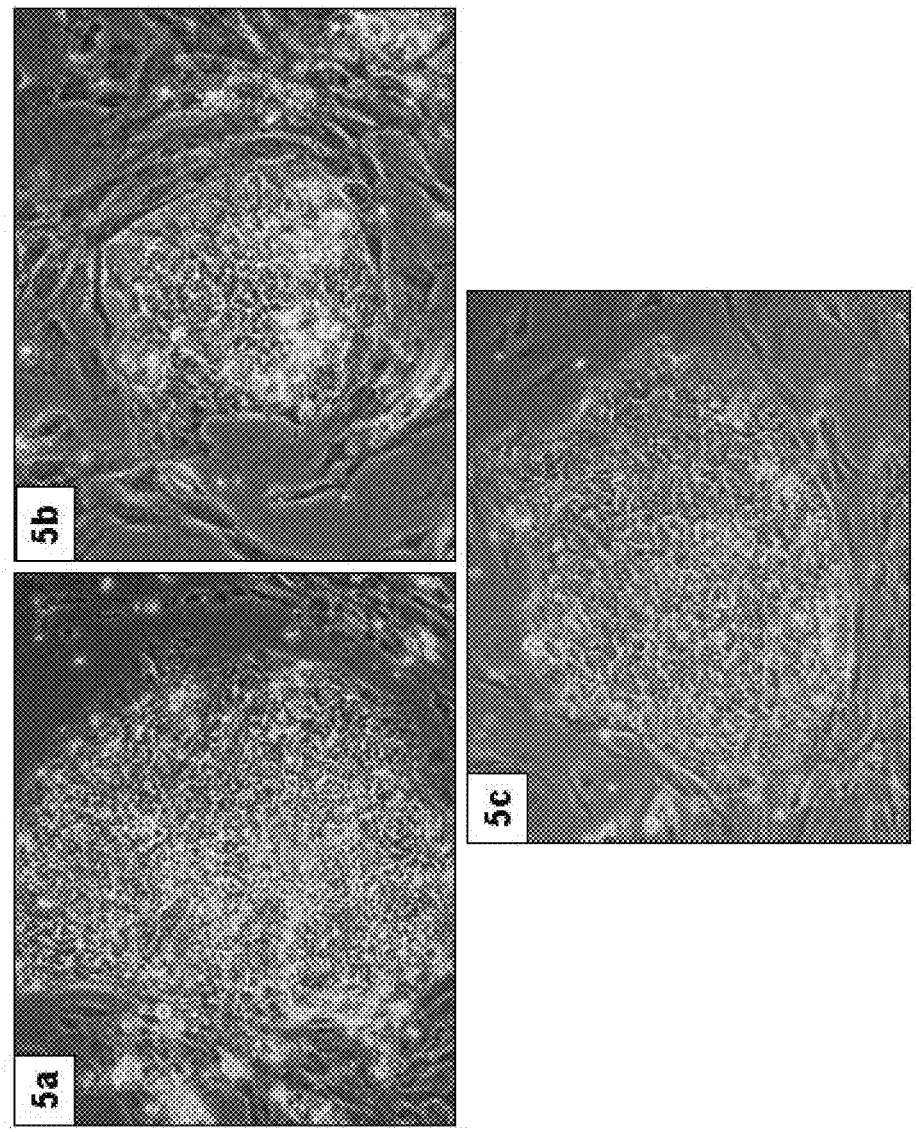
Figs. 5a-c

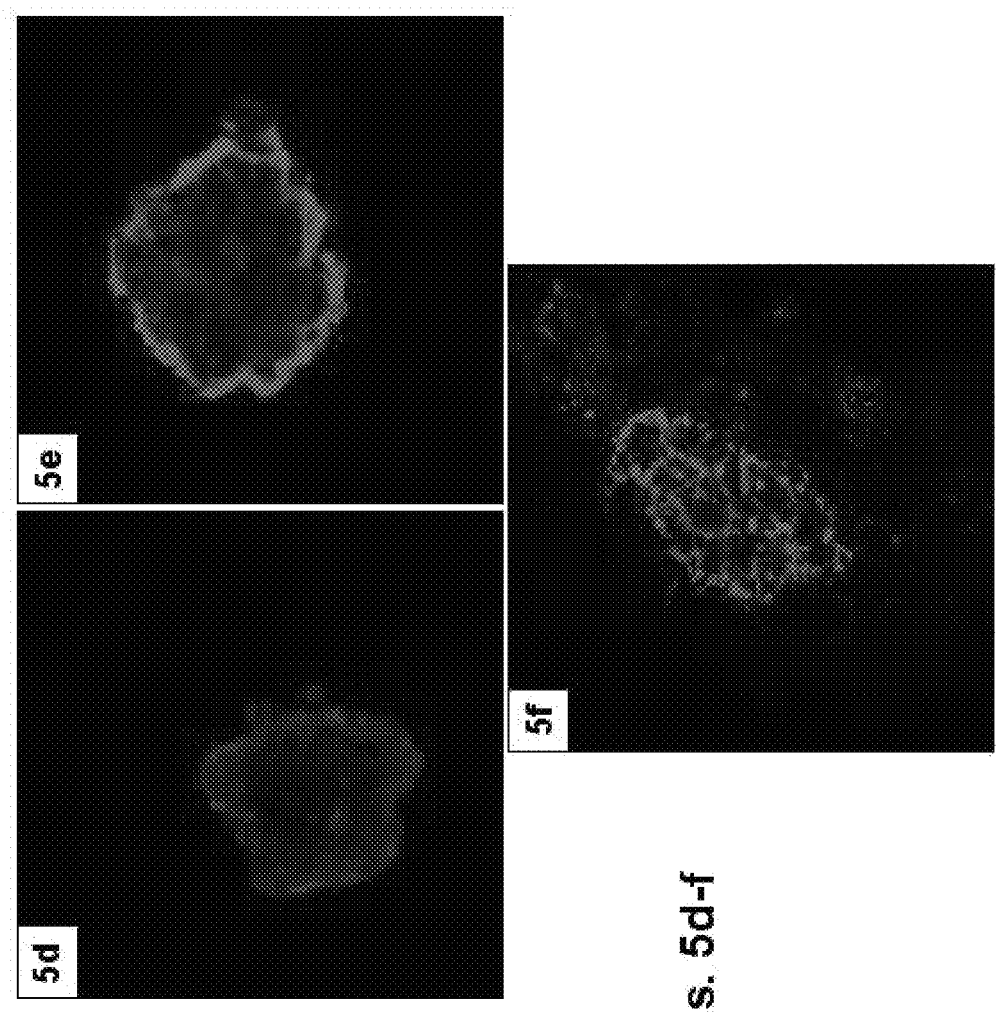
Figs. 5d-f

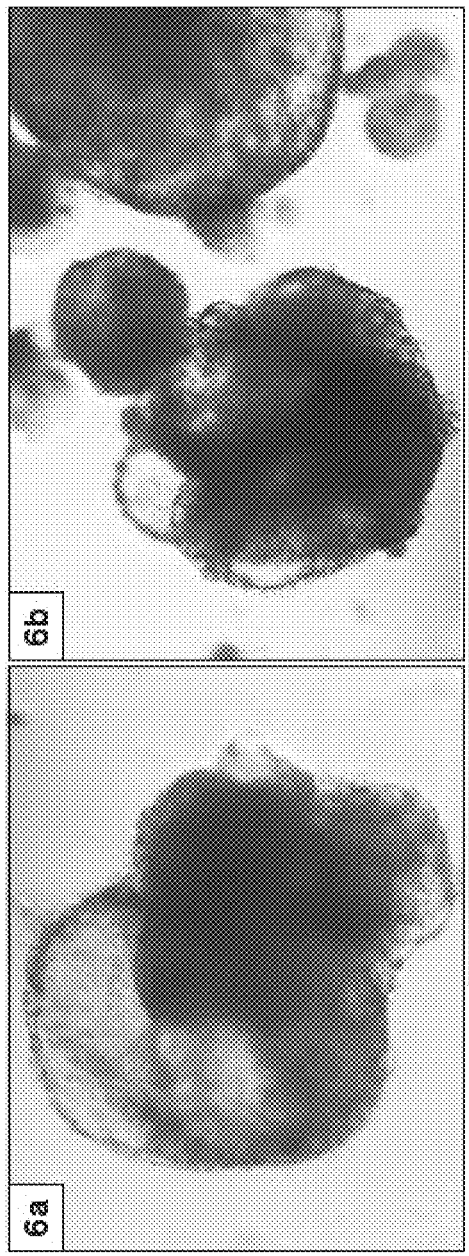
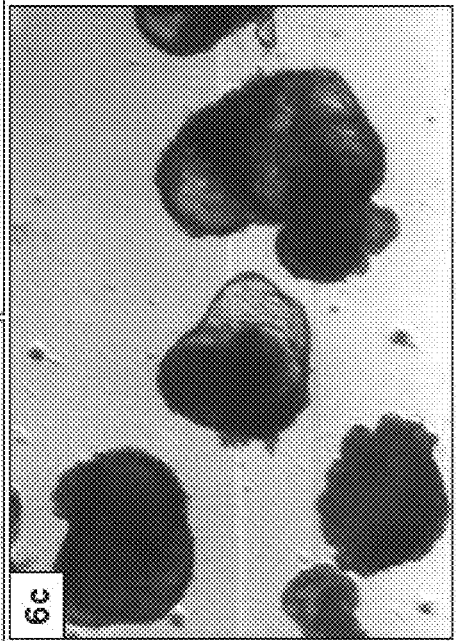
Figs. 6a-c

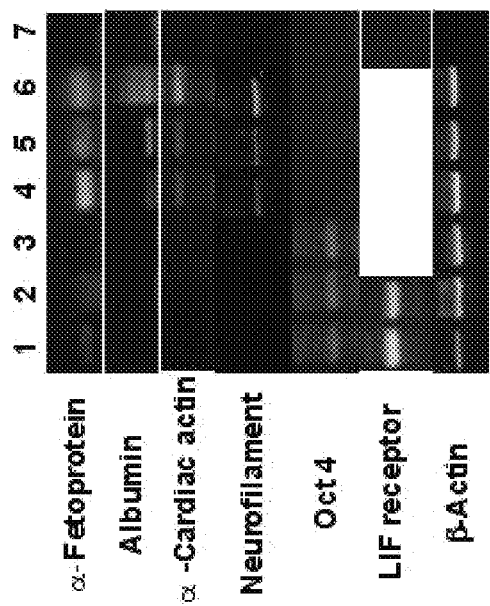

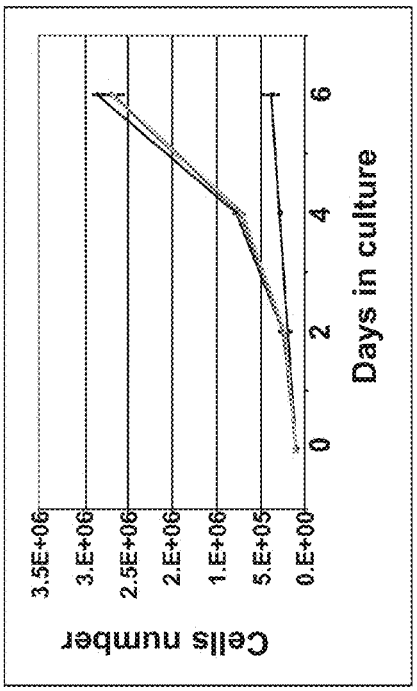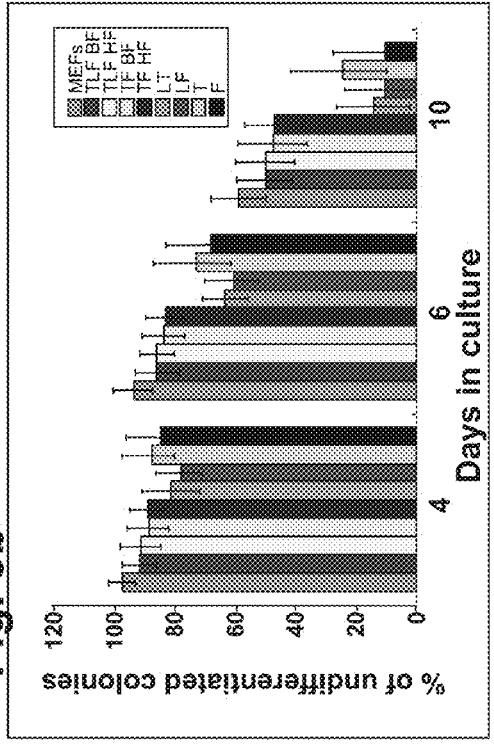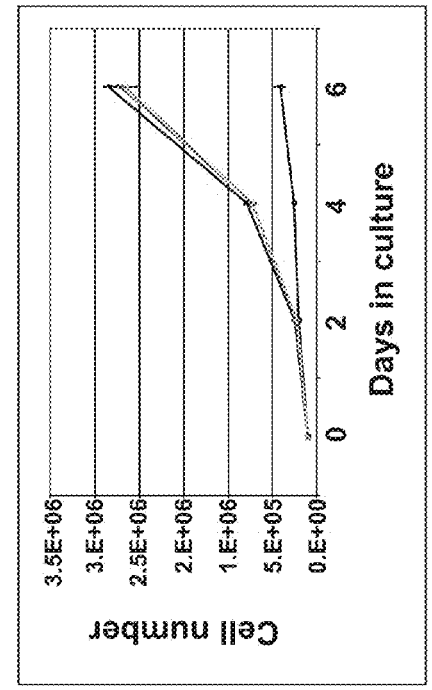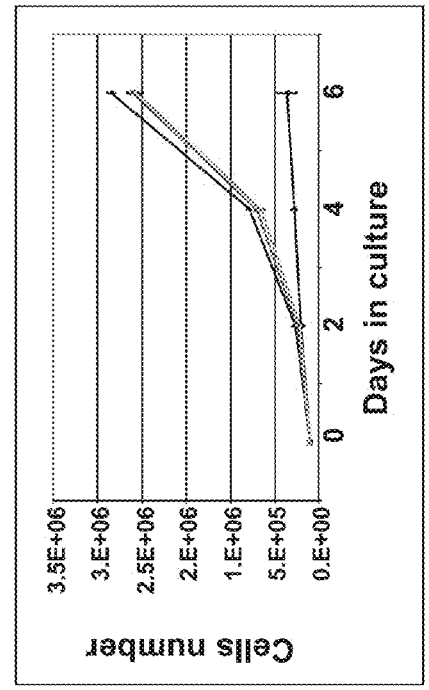
Figs. 8a-d
Fig. 8a
Fig. 8b
Fig. 8c
Fig. 8d

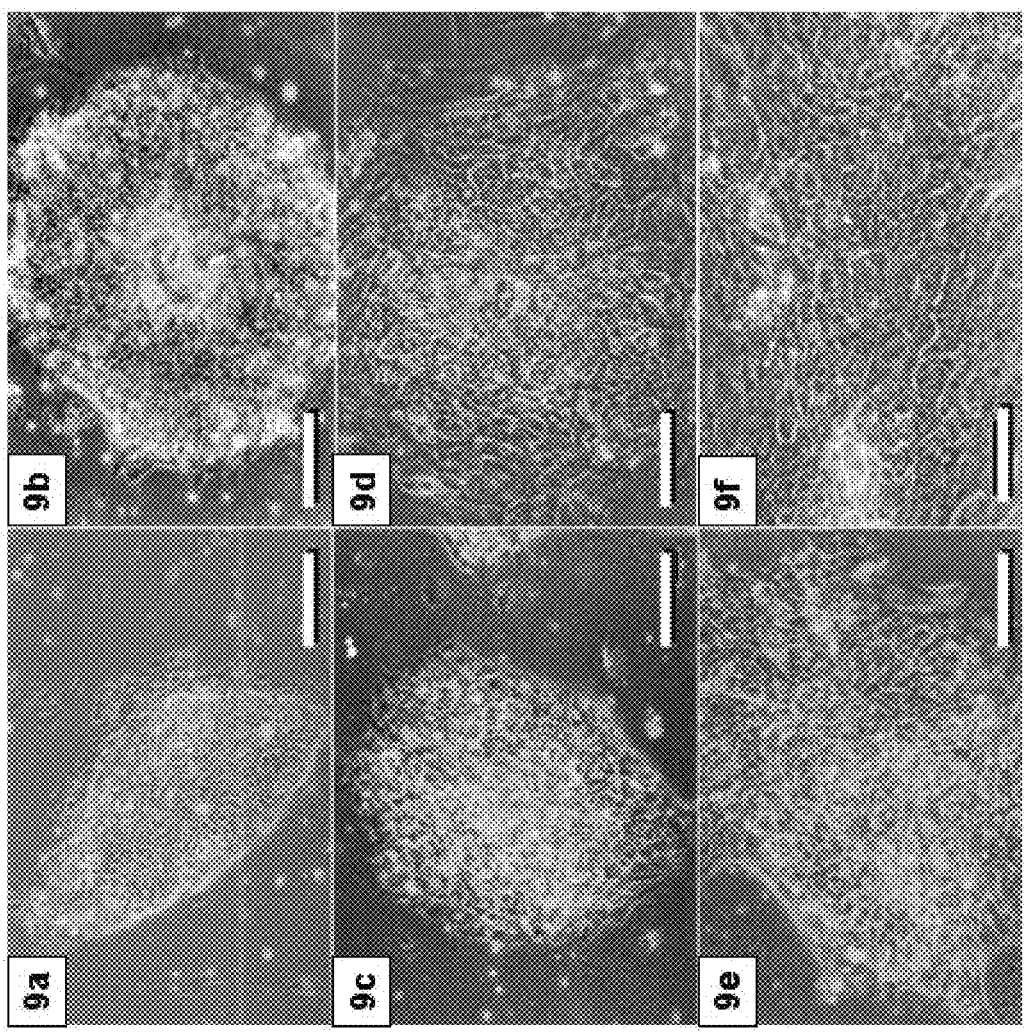
Figs. 9a-f

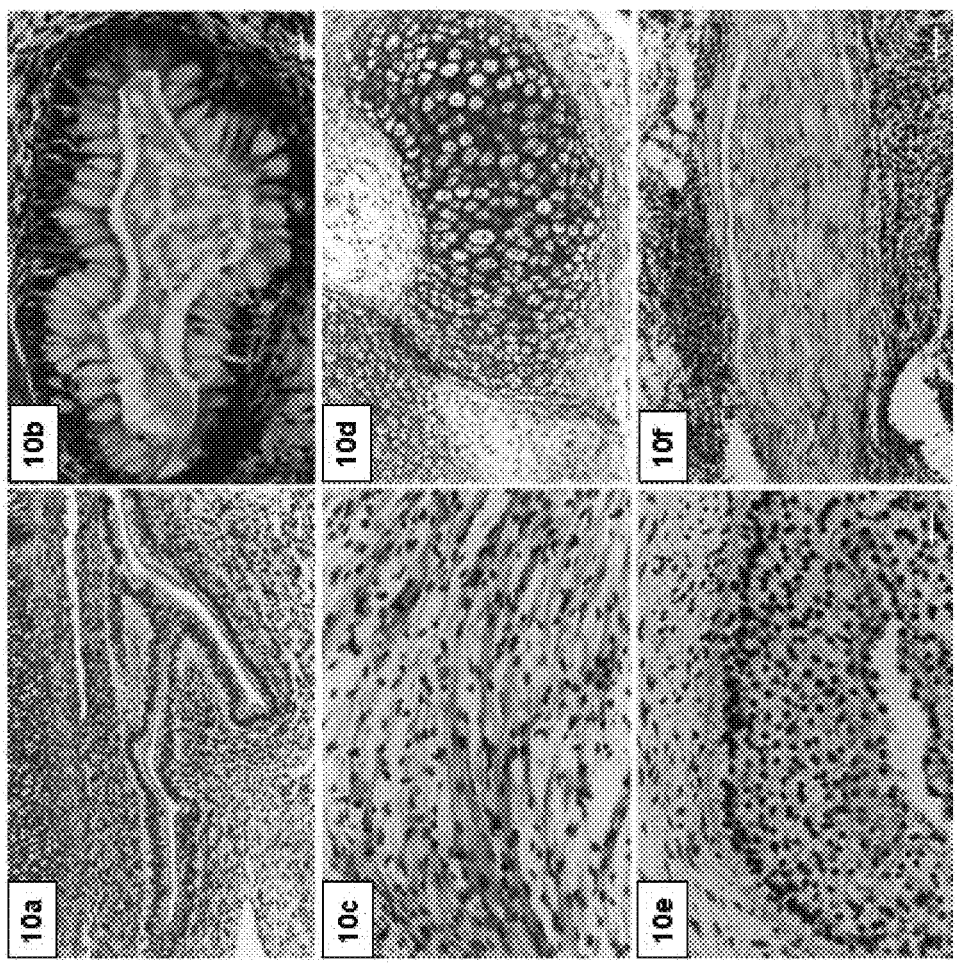
Figs. 10a-f

SEQUENCE LISTING

<160> NUMBER OF SEQ ID NOS: 14

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
gagaacaatg agaaccttca gga                23

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
ttctggcgcc ggttacagaa cca                23

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 3
tgcttgaatg tgctgatgac aggg               24

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
aaggcaagtc agcagccatc tcat               24

<210> SEQ ID NO 5
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 5
gctggattgt ctgcaggatg gggaa              25

<210> SEQ ID NO 6
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 6
tcccctgaag aaaattggtt aaaat              25

<210> SEQ ID NO 7
<211> LENGTH: 22
<212> TYPE: DNA
<213> ORGANISM: Artificial sequence

```
<220> FEATURE:
<223> OTHER INFORMATION: Single strand DNA oligonucleotide

<400> SEQUENCE: 7
gagtgaaatg gcacgatacc ta                                              22

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
tttcctctcc ttcttcacct tc                                              22

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
ggagttatgg tgggtatggg tc                                              22

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
agtggtgaca aaggagtagc ca                                              22

<210> SEQ ID NO 11
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 11
caaaagagtg tctgtgag                                                   18

<210> SEQ ID NO 12
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 12
ccatgtattt acattggc                                                   18

<210> SEQ ID NO 13
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 13
atctggcacc acaccttcta caatgagctg cg                                   32
```

```
<210> SEQ ID NO 14
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 14
cgtcatactc ctgcttgctg atccacatct gc                                32
```

MEDIUM COMPRISING TRANSFORMING GROWTH FACTOR BETA 1 AND BASIC FIBROBLAST GROWTH FACTOR

RELATED APPLICATIONS

This application is a continuation of U.S. patent application Ser. No. 14/578,443 filed on Dec. 21, 2014, which is a continuation of U.S. patent application Ser. No. 14/058,347 filed on Oct. 21, 2013, now U.S. Pat. No. 8,945,925, which is a continuation of U.S. patent application Ser. No. 13/466,161 filed on May 8, 2012, now U.S. Pat. No. 8,563,311, which is a continuation of U.S. patent application Ser. No. 13/083,630 filed on Apr. 11, 2011, now U.S. Pat. No. 8,222,034, which is a division of U.S. patent application Ser. No. 12/585,646 filed on Sep. 21, 2009, now U.S. Pat. No. 7,955,851, which is a continuation of U.S. patent application Ser. No. 10/537,784 filed on Jun. 6, 2005, now U.S. Pat. No. 7,592,175, which is a National Phase of PCT Patent Application No. PCT/IL03/01030 having International Filing Date of Dec. 7, 2003, which claims the benefit of U.S. Provisional Patent Application No. 60/433,619 filed on Dec. 16, 2002.

The contents of the above applications are all incorporated by reference as if fully set forth herein in their entirety.

SEQUENCE LISTING STATEMENT

The ASCII file, entitled 66810SequenceListing.txt, created on Jul. 4, 2016, comprising 3,382 bytes, submitted concurrently with the filing of this application is incorporated herein by reference.

FIELD AND BACKGROUND OF THE INVENTION

The present invention relates to methods of preparing human embryonic stem cell lines using feeder cells (e.g., feeder cell layer, also known as feeder layer)-free, xeno-free culture systems and of stem cells which are capable of being maintained in an undifferentiated, pluripotent and proliferative state in culture which is free of xeno contaminants and feeder cells.

Embryonic stem cells (ESCs), being totipotent, have the potential to develop into any type of cell and to generate any type of tissue, organ or body part, including a whole organism. As such, it is expected that the ability to provide normal clonal human ESCs on demand and to manipulate the differentiation thereof will provide a powerful tool capable of driving radical advances in the biomedical, industrial and scientific fields. Potential applications of ESCs are far ranging and include drug discovery and testing, generation of cells, tissues and organs for use in transplantation, production of biomolecules, testing the toxicity and/or teratogenicity of compounds and facilitating the study of developmental and other biological processes. For example, diseases presently expected to be treatable by therapeutic transplantation of ESCs or ESC-derived cells include Parkinson's disease, cardiac infarcts, juvenile-onset diabetes mellitus, and leukemia (Gearhart J. Science 1998, 282:1061; Rossant and Nagy, Nature Biotech. 1999, 17:23).

There are, however, significant hurdles to the practical exploitation of human ESCs.

In order to maintain human ESC in an undifferentiated state ES cultures must be supplemented with factors which maintain cell proliferation, inhibit ES cell differentiation and preserve pluripotency.

In addition, for cell replacement and tissue regeneration therapies human ESCs must be cultured in a complete animal-free environment and in the presence of well-defined culturing conditions which enable a complete reproduction of ES cultures.

Currently practiced ES culturing methods are mainly based on the use of feeder cell layers which secrete factors needed for stem cell proliferation, while at the same time, inhibit their differentiation. Feeder cell free systems have also been used in ES cell culturing, such systems utilize matrices supplemented with serum, cytokines and growth factors as a replacement for the feeder cell layer.

Feeder-layer Based Cultures

Mouse Feeder Layers—The most common method for culturing ES cells is based on mouse embryonic fibroblasts (MEF) as a feeder cell layer supplemented with tissue culture medium containing serum or leukemia inhibitor factor (LIF) which supports the proliferation and the pluripotency of the ES cells [Thomson J A, Itskovitz-Eldor J, Shapiro S S, Waknitz M A, Swiergiel J J, Marshall V S, Jones J M. (1998). Embryonic stem cell lines derived from human blastocysts. Science 282: 1145-7; Reubinoff B E, Pera M F, Fong C, Trounson A, Bongso A. (2000). Embryonic stem cell lines from human blastocysts: somatic differentiation in vitro. Nat. Biotechnol. 18: 399-404]. MEF cells are derived from day 12-13 mouse embryos in medium supplemented with fetal bovine serum. Under these conditions mouse ES cells can be maintained in culture as pluripotent stem cells, preserving their phenotypical and functional characteristics. However, unlike mouse ES cells, the presence of exogenously added LIF does not prevent differentiation of human ES cells (Thomson et al., 1998, Science 282: 1145-7; Reubinoff et al., 2000, Nat. Biotechnol. 18: 399-404). Furthermore, the use of feeder cells substantially increases the cost of production, and makes scale-up of human ES cell culture impractical. Additionally, the feeder cells are metabolically inactivated to keep them from outgrowing the stem cells, hence it is necessary to have fresh feeder cells for each splitting of human ES culture. Since at present, the separation of feeder cell components from embryonic cells prepared in bulk culture cannot be efficiently achieved, feeder cell layer-prepared ES cultures are not suitable for human therapy.

ES cells can also be cultured on MEF under serum-free conditions using serum replacement supplemented with basic fibroblast growth factor (bFGF) [Amit M, Carpenter M K, Inokuma M S, Chiu C P, Harris C P, Waknitz M A, Itskovitz-Eldor J, Thomson J A. (2000). Clonally derived human embryonic stem cell lines maintain pluripotency and proliferative potential for prolonged periods of culture. Dev. Biol. 227: 271-8]. Under these conditions the cloning efficiency of ES cells is 4 times higher than under fetal bovine serum. In addition, following 6 months of culturing under serum replacement the ES cells still maintain their pluripotency as indicated by their ability to form teratomas which contain all three embryonic germ layers. Although this system uses a better-defined culture conditions, the presence of mouse cells in the culture exposes the human culture to pathogens which restricts their use in cell-based therapy.

Human embryonic fibroblasts or adult fallopian epithelial cells as feeder cell layers—Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6]. However, the major disadvantage of using human embryonic fibroblasts or adult fallopian tube epithelial cells as feeder cells is that both of these cell lines have a limited passage capacity of only 8-10 times, thereby limiting the ability of a prolonged ES growth period. For a prolonged culturing period, the ES cells must be grown on human feeder cells originated from several subjects which results in an increased variability in culture conditions.

Foreskin feeder layers—Human ES cells can be cultured on human foreskin feeder layer as disclosed in U.S. patent application Ser. No. 10/368,045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers. In addition, unlike human fallopian epithelial cells or human embryonic fibroblasts, human ES cells cultured on foreskin feeder layers were maintained in culture in a pluripotent and undifferentiated state for at least 87 passages. However, although foreskin cells can be maintained in culture for long periods (i.e., 42 passages), the foreskin culture system is not well-defined due to differences between separate batches. In addition, human feeder layer-based culture systems would still require the simultaneous growth of both feeder layers and hES cells. Therefore, feeder cells-free culturing systems have been developed.

Feeder Cells-free Cultures

Stem cells can be grown on a solid surface such as an extracellular matrix (e.g., Matrigel® or laminin) in the presence of a culture medium. Unlike feeder-based cultures which require the simultaneous growth of feeder cells and stem cells and which may result in mixed cell populations, stem cells grown on feeder cells-free systems are easily separated from the surface. The culture medium used for growing the stem cells contains factors that effectively inhibit differentiation and promote their growth such as MEF-conditioned medium and bFGF. However, commonly used feeder cells-free culturing systems utilize an animal-based matrix (e.g., Matrigel®) supplemented with mouse or bovine serum, or with MEF conditioned medium [Xu C, et al. (2001). Feeder cells-free growth of undifferentiated human embryonic stem cells. Nat Biotechnol. 19: 971-4] which present the risk of animal pathogen cross-transfer to the human ES cells, thus compromising future clinical applications.

As is further disclosed in U.S. patent application Ser. No. 10/368,045, stem cells can be cultured on a matrix surface supplemented with foreskin-derived conditioned medium. However, this medium, although present an animal-free system is yet not fully-defined in terms of culture composition.

Recent attempts to culture human embryonic stem cells on a more defined culture composition utilized Matrigel or laminin surfaces and a mixture of growth factors. However, as disclosed in U.S. Pat Appl. No. 20030017589 under these conditions only 50-70% of the cells exhibited undifferentiated cell morphology. In addition, the stem cells further exhibited a relatively short doubling time of 19 hours, which suggests that the stem cells became tumorigenic (see Amit et al, 2000, Dev. Biol. 227: 271-8).

There is thus a widely recognized need for, and it would be highly advantageous to have, a feeder cells-free, xeno-free culturing system, capable of maintaining human ES cells in a proliferative, pluripotent and undifferentiated state devoid of the above limitations.

SUMMARY OF THE INVENTION

According to one aspect of the present invention there is provided a method of establishing a feeder cells-free human embryonic stem cell line capable of being maintained in an undifferentiated, pluripotent and proliferative state, the method comprising: (a) obtaining human embryonic stem cells, and (b) culturing the human embryonic stem cells under culturing conditions devoid of feeder cells and including a matrix and a tissue culture medium supplemented with $TGF\beta_1$, bFGF and/or LIF to thereby obtain the feeder cells-free human embryonic stem cell line.

According to further features in the described preferred embodiments the method further comprising cloning a cell from the human embryonic stem cell line resultant from step (b) under the culturing conditions.

According to another aspect of the present invention there is provided a method of propagating a human embryonic stem cell line in an undifferentiated, pluripotent and proliferative state under culturing conditions devoid of feeder cells, the method comprising culturing cells of the human embryonic stem cell line on a matrix and a tissue culture medium supplemented with $TGF\beta_1$, bFGF and/or LIF to thereby maintain the cells of the human embryonic stem cell line in an undifferentiated, pluripotent and proliferative state.

According to yet another aspect of the present invention there is provided a method of establishing a feeder cells-free human embryonic stem cell line capable of being maintained in an undifferentiated, pluripotent and proliferative state, the method comprising: (a) obtaining human embryonic stem cells, and (b) culturing the human embryonic stem cells under culturing conditions devoid of feeder layer cells and including a fibronectin matrix and a tissue culture medium supplemented with $TGF\beta_1$, bFGF and/or LIF to thereby obtain the feeder cells-free human embryonic stem cell line.

According to still another aspect of the present invention there is provided a method of propagating a human embryonic stem cell line in an undifferentiated, pluripotent and proliferative state under culturing conditions devoid of feeder cells, the method comprising culturing cells of the human embryonic stem cell line on a fibronectin matrix and a tissue culture medium supplemented with $TGF\beta_1$, bFGF and/or LIF to thereby maintain the cells of the human embryonic stem cell line in an undifferentiated, pluripotent and proliferative state.

According to an additional aspect of the present invention there is provided a method of establishing a xeno-free, feeder cells-free embryonic stem cell line of a species capable of being maintained in an undifferentiated, pluripotent and proliferative state, the method comprising: (a) obtaining embryonic stem cells, and (b) culturing the embryonic stem cells under culturing conditions devoid of feeder cells and xeno contaminants and including a species-derived matrix and a tissue culture medium to thereby obtain the xeno-free, feeder cells-free embryonic stem cell line of the species.

According to yet an additional aspect of the present invention there is provided a method of propagating a species embryonic stem cell line in an undifferentiated, pluripotent and proliferative state under culturing conditions devoid of feeder cells and xeno contaminants, the method comprising culturing cells of the species embryonic stem cell line on a species-derived matrix and a tissue culture medium to thereby maintain the cells of the species embryonic stem cell line in an undifferentiated, pluripotent and proliferative state.

According to an additional aspect of the present invention there is provided a cell culture comprising undifferentiated, pluripotent and proliferative human embryonic stem cells in a culture medium, wherein the cell culture is substantially free of xeno- and/or feeder cells contaminants.

According to a further aspect of the present invention there is provided a xeno-free, feeder cells-free culture system comprising a matrix and a tissue culture medium, the xeno-free, feeder cells-free culture system being selected capable of maintaining human embryonic stem cells cultured therein in a proliferative, pluripotent and undifferentiated state.

According to yet a further aspect of the present invention there is provided a method of treating an individual in need of cell replacement and/or tissue regeneration, comprising administering a human embryonic stem cell preparation being free of xeno and feeder cells contaminants to the individual.

According to further features in the described preferred embodiments the method further comprising preparing the human embryonic stem cell preparation prior to the administering, the preparing being effected by: (a) obtaining human embryonic stem cells, and (b) culturing the human embryonic stem cells under culturing conditions devoid of feeder cells and xeno contaminants and including a human-derived fibronectin matrix and a tissue culture medium supplemented with $TGF\beta_1$, bFGF and/or LIF to thereby prepare the human embryonic stem cell preparation.

According to still a further aspect of the present invention there is provided a method of maintaining human embryonic stem cells in an undifferentiated, pluripotent and proliferative state under culturing conditions devoid of feeder cells, the method comprising culturing the human embryonic stem cells under culturing conditions including a matrix and tissue culture medium supplemented with at least one growth factor provided at a concentration range selected capable of maintaining the stem cells for at least 56 passages with a doubling time of at least 25 hours.

According to still further features in the described preferred embodiments the matrix is a fibronectin matrix.

According to still further features in the described preferred embodiments the fibronectin is selected from the group consisting of bovine fibronectin, recombinant bovine fibronectin, human fibronectin, recombinant human fibronectin, mouse fibronectin, recombinant mouse fibronectin, and synthetic fibronectin.

According to still further features in the described preferred embodiments the culturing conditions are substantially free of xeno contaminant and whereas the matrix is selected from the group consisting of human plasma fibronectin matrix, recombinant human plasma fibronectin matrix, human cellular fibronectin matrix, recombinant human cellular fibronectin matrix, synthetic fibronectin.

According to still further features in the described preferred embodiments the human embryonic stem cell line comprises at least 85% of undifferentiated human embryonic stem cells.

According to still further features in the described preferred embodiments the cells of the human embryonic stem cell line maintain a doubling time of at least 25 hours.

According to still further features in the described preferred embodiments the tissue culture medium further includes serum and/or serum replacement.

According to still further features in the described preferred embodiments the serum and/or the serum replacement is provided at a concentration of at least 10%.

According to still further features in the described preferred embodiments the serum and/or the serum replacement is provided at a concentration of 15%.

According to still further features in the described preferred embodiments the $TGF\beta_1$ is provided at a concentration of at least 0.06 ng/ml.

According to still further features in the described preferred embodiments the $TGF\beta_1$ is provided at a concentration of 0.12 ng/ml.

According to still further features in the described preferred embodiments the bFGF is provided at a concentration of at least 2 ng/ml.

According to still further features in the described preferred embodiments the bFGF is provided at a concentration of 4 ng/ml.

According to still further features in the described preferred embodiments the LIF is provided at a concentration of at least 500 u/ml.

According to still further features in the described preferred embodiments the LIF is provided at a concentration of 1000 u/ml.

According to still further features in the described preferred embodiments the matrix is a species-derived fibronectin matrix.

According to still further features in the described preferred embodiments the feeder cells-free culturing conditions are substantially free of xeno contaminants.

According to still further features in the described preferred embodiments the cells of the species embryonic stem cell line maintain a doubling time of at least 20 hours.

According to still further features in the described preferred embodiments the tissue culture medium includes a species-derived serum and/or a serum replacement.

According to still further features in the described preferred embodiments the species-derived serum is provided at a concentration of at least 5%.

According to still further features in the described preferred embodiments the tissue culture medium further includes at least one growth factor.

According to still further features in the described preferred embodiments the at least one growth factor is selected from the group consisting of $TGF\beta_1$, bFGF, LIF.

According to still further features in the described preferred embodiments the tissue culture medium is a species-derived conditioned medium.

According to still further features in the described preferred embodiments the human embryonic stem cells are maintainable in an undifferentiated, pluripotent and proliferative state for at least passage 38.

According to still further features in the described preferred embodiments the $TGF\beta_1$ is provided at a concentration range of 0.06-0.24 ng/ml.

According to still further features in the described preferred embodiments the bFGF is provided at a concentration range of 2-8 ng/ml.

According to still further features in the described preferred embodiments the LIF is provided at a concentration range of 500-2000 u/ml.

According to still further features in the described preferred embodiments the culturing conditions include serum replacement at a concentration of 15%, $TGF\beta_1$ at a concentration of 0.12 ng/ml, LIF at a concentration of 1000 u/ml, and bFGF at a concentration of 4 ng/ml.

The present invention successfully addresses the shortcomings of the presently known configurations by providing methods of establishing and propagating human embryonic stem cell lines using feeder cells-free, xeno-free culture systems and stem cells which are capable of being maintained in an undifferentiated, pluripotent and proliferative state in culture which is free of xeno contaminants and feeder cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
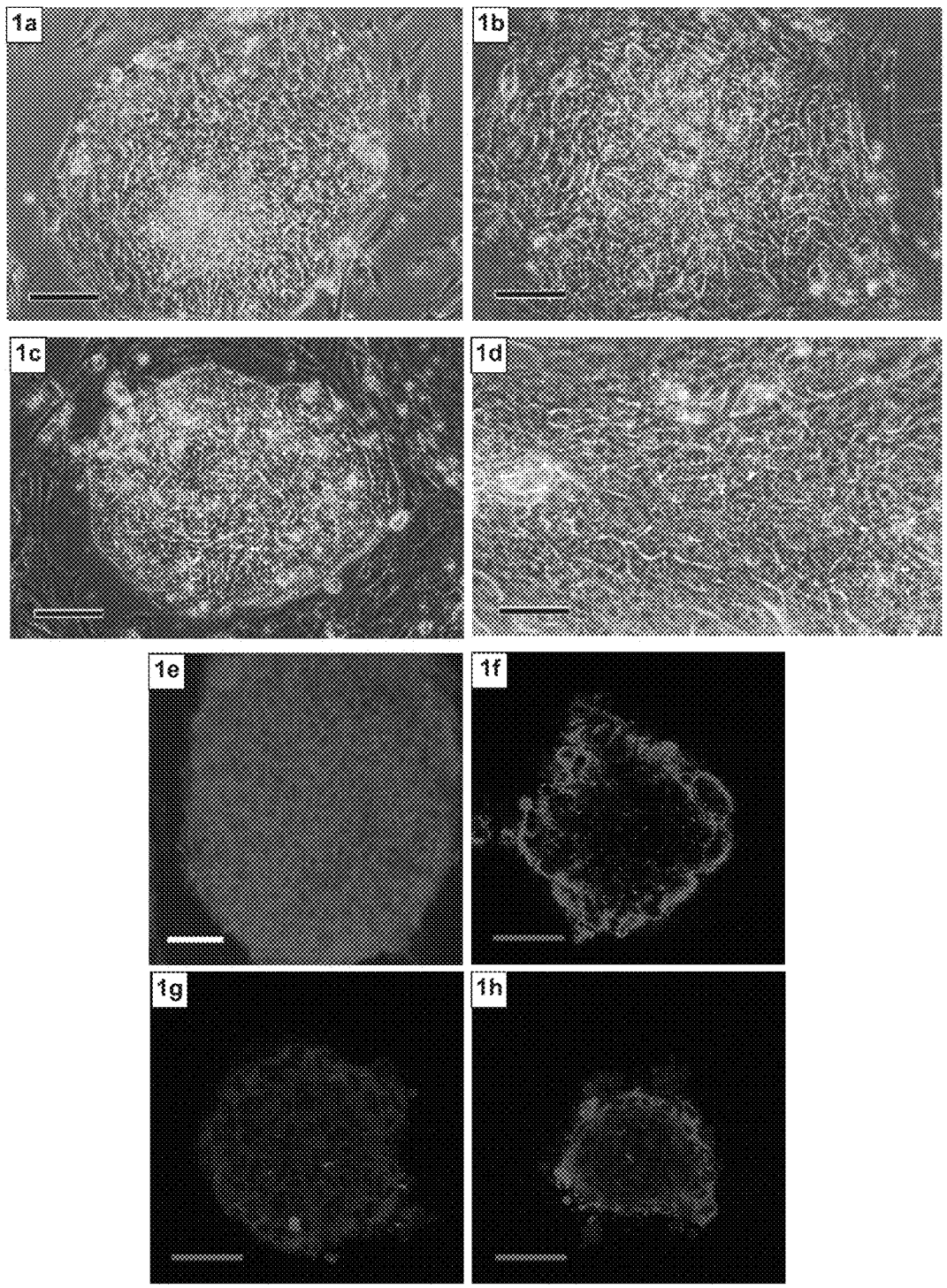

FIGS. 1a-1d are micrographs illustrating ES cell colonies and ES single cells grown on a bovine-derived fibronectin matrix in a feeder cells-free system. Shown are bright field images of the various ES cell lines grown on fibronectin in the presence of serum replacement and various combinations of growth factors. FIG. 1a—I-6 ES cell line grown in the presence of $TGF\beta_1$, LIF and bFGF (TLF) for 31 passages (size bar represents 100 μM); FIG. 1b—I-3 ES cell line grown in TLF for 21 passages (size bar represents 50 μM); FIG. 1c—I-6 ES cell line grown in TLF for 31 passages (size bar represents 50 μM); FIG. 1d—I-3 ES cell line grown in $TGF\beta_1$ and bFGF (TF) for 20 passages (size bar represents 38 μM). Note the spaces between the cells (FIGS. 1a-c) and the high nucleus-to-cytoplasm ratio typical of human ES cells (FIG. 1d).

FIGS. 1e-1h are immunohistochemistry micrographs illustrating the expression of surface markers typical of undifferentiated cells on the human I-3 and I-6 ES cell lines grown on a bovine-derived fibronectin matrix in a feeder cells-free system. Shown are fluorescent images of human ES cells (line I-3) grown in the presence of TF for 17 passages and labeled with anti-SSEA4 antibodies (FIG. 1e, size bar represents 50 μM), I-3 ES cells grown in the presence of TLF for 38 passages and labeled with anti-SSEA4 antibodies (FIG. 1f, size bar represents 6 μM), I-6 ES cells grown in the presence of TLF for 30 passages and labeled with anti-TRA-60 antibodies (FIG. 1g, size bar represents 6 μM), I-3 ES cells grown in the presence of TF for 21 passages and labeled with anti-TRA-81 antibodies (FIG. 1h, size bar represents 6 μM). The fluorescent images were captured using either an inverted fluorescent microscope (FIG. 1e) or a confocal microscope (FIGS. 1f-h).

Figure 2:
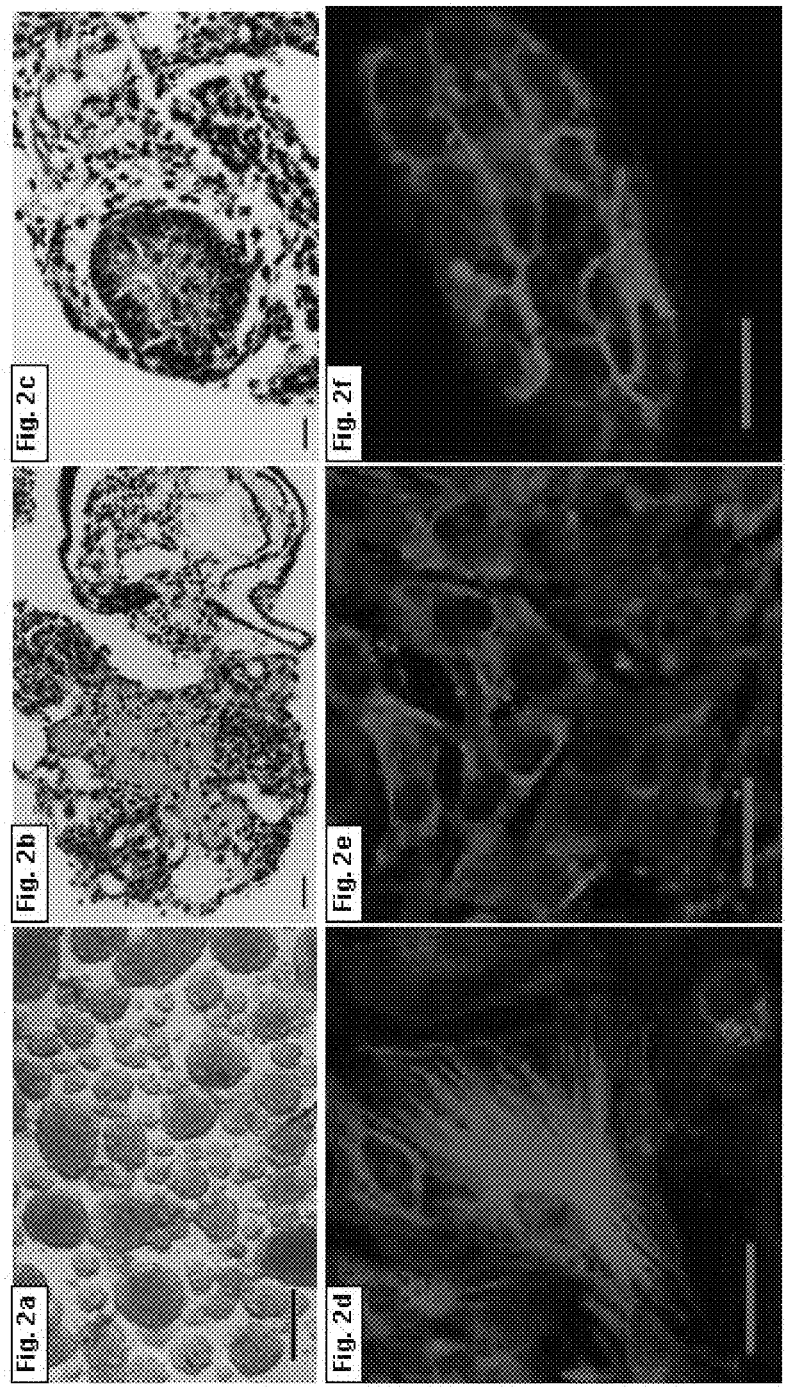

FIGS. 2a-2c illustrate the in vitro differentiation of hES cells grown on a bovine-derived fibronectin matrix in a feeder cells-free system. Shown are histological sections of EBs derived from cells grown in the feeder cells-free culture system. FIG. 2a—a 24-hour-old simple EB derived from I-3 cell line after being grown for 28 passages in TF (size bar represents, 100 μM); FIG. 2b—a 14-day-old EB derived from I-3 cell line grown for 28 passages in TF (size bar represents 50 μM); FIG. 2c—a 14-day-old EB derived from cell line I-3 grown for 30 passages in TLF (size bar represents 25 μM). Note the external protective epithelium (FIG. 2b, arrow) of the EB and the ball-like structure consisting of columnar epithelium surrounded by mesenchymal tissue (FIG. 2c).

FIGS. 2d-2f illustrate the expression of representative markers of mesoderm and ectoderm in cells derived from 14-day-old EBs formed from ES cells grown in various media in a bovine-derived fibronectin matrix in a feeder cells-free system of the present invention. EB cells derived from various ES cell lines were fluorescently immunostained with various antibody probes. FIG. 2d—the I-6 cell line grown in TLF for 22 passages and immunostained using antibodies directed against neural specific tubulin (size bar represents 6 μM). FIG. 2e—the I-3 cell line grown in TLF for 30 passages and immunostained using antibodies directed against the smooth muscle actin (size bar represents 6 μM). FIG. 2f—the I-3 cell line grown in TF for 28 passages and immunostained using antibodies directed against CD-31 (size bar represents 6 μM).

Figure 3:
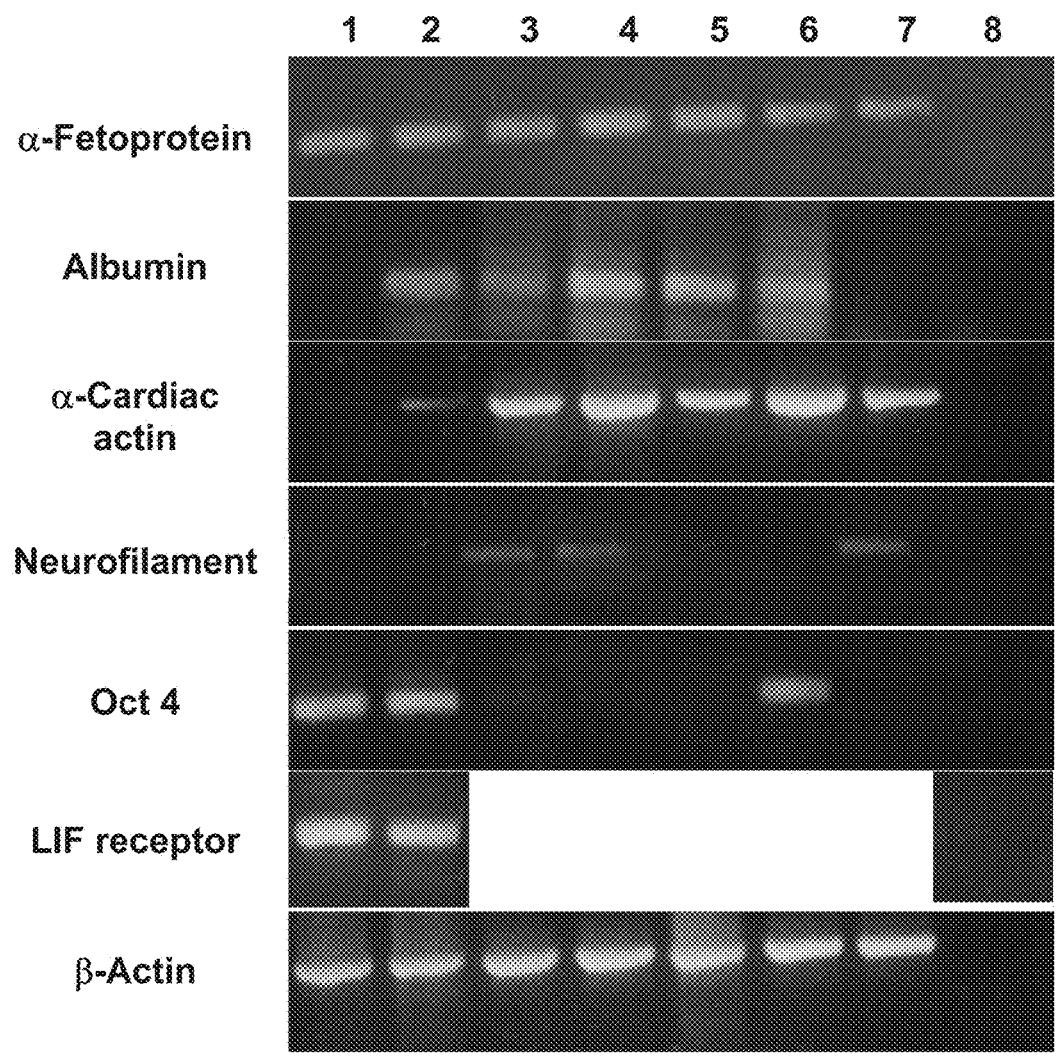

FIG. 3 illustrates RT-PCR determination of the differentiation stage of the I-3 or I-6 ES cells grown on a bovine-derived fibronectin matrix in a feeder cells-free system and of the embryoid bodies (EBs) derived therefrom. The RT-PCR reaction was performed on RNA samples extracted from I-3, I-6 ES cells or EBs derived therefrom. Lane 1—I-3 ES cells grown in TF for 19 passages; lane 2—I-3 ES cells grown in TLF for 20 passages; lane 3—14-day-old EBs derived from I-3 ES cells grown in TLF for 23 passages; lane 4—14-day-old EBs derived from I-3 ES cells grown in TF for 28 passages; lane 5—14-day-old EBs derived from I-3 ES cells grown in TLF for 30 passages; lane 6—14-day-old EBs derived from I-3 ES cells grown in TLF for 29 passages; lane 7—14-day-old EBs derived from I-6 ES cells grown in TLF for 22 passages. The specificity of the reaction was verified in the absence of RNA (FIG. 3, lane 8). Note that the EBs samples of lanes 3-6 were derived from four different batches of I-3 ES cells.

FIGS. 4a-4c illustrate histological sections of teratomas derived from the I-3 and I-6 ES cell lines grown for 26 and 19 passages, respectively, in TLF on a bovine-derived fibronectin matrix in a feeder cells-free system. Teratoma sections include myelinated nerve (FIG. 4a), details of hyaline cartilage (FIG. 4b) and secretory epithelium rich in goblet cells (FIG. 4c). Size bar represents 25 μM.

FIGS. 5a-5c are morphology micrographs illustrating ES cell colonies grown on a human-derived fibronectin matrix in a feeder cells-free system. Shown are bright field images of the I-3 ES cell line grown on human cellular fibronectin for 22 passages in the presence of serum replacement and the TF combination of growth factors.

FIGS. 5d-5f are immunohistochemistry micrographs illustrating the expression of surface markers typical of undifferentiated cells on human I-3 and H-9 ES cell lines grown on a human-derived fibronectin matrix in a feeder cells-free system. Shown are fluorescent images of human I-3 ES cell line cultured on human cellular fibronectin in the presence of TF for 16 passages and labeled with anti-TRA-1-60 antibodies (FIG. 5d) or anti-TRA-1-81 (FIG. 5e), the human H-9 ES cell line cultured on human plasma fibronectin in the presence of TLF for 10 passages and labeled with anti-SSEA4 (FIG. 5f).

FIGS. 6a-6c illustrate the in vitro differentiation of hES cells grown on a human fibronectin matrix under xeno-free, feeder cells-free conditions. Shown are images of 14-day-old EBs derived from the I-3 ES cells grown under various culturing conditions. FIG. 6a—human cellular fibronectin matrix in the presence of the TLF growth factors for 17 passages; FIG. 6b—human cellular fibronectin matrix in the presence of the TF growth factors for 17 passages; FIG. 6c—human plasma fibronectin matrix in the presence of the TLF growth factors for 16 passages.

FIG. 7 illustrates RT-PCR determination of the differentiation stage of the I-3 ES cells grown on a human-derived fibronectin matrix in a feeder cells-free system and of the embryoid bodies (EBs) derived therefrom. The RT-PCR reaction was performed on RNA samples extracted from I-3 ES cells or EBs derived therefrom. Lane 1—I-3 ES cells grown in TF for 22 passages; lane 2—I-3 ES cells grown in TLF for 18 passages; lane 3—I-3 ES cells grown in TLF for 17 passages; lane 4—14-day-old EBs derived from I-3 ES cells grown in TF for 17 passages; lane 5—14-day-old EBs derived from I-3 ES cells grown in TLF for 17 passages; lane 6—14-day-old EBs derived from I-3 ES cells grown in TLF for 16 passages; The specificity of the reaction was verified in the absence of RNA (FIG. 7, lane 7).

FIGS. 8a-8c illustrate growth rates of the I-3 (FIG. 8a), I-6 (FIG. 8b) and H-9 (FIG. 8c) hES cell lines under various culturing conditions. Shown are the growth rates of the I-3, I-6 and H-9 hES cell lines when cultured on the bovine-fibronectin matrices in the presence of the TLF (FIGS. 8a, b, and c, respectively, pink curves) or the TF (FIGS. 8a, b, and c, respectively, black curves) combinations of growth factors, on the human-fibronectin matrix in the presence of the TF combination of growth factors (FIGS. 8 a, b, and c, respectively, light blue curves), or on the MEFs feeder cells (FIGS. 8 a, b, and c, respectively, dark blue curves).

FIG. 8d is a bar graph illustrating the capacity of various culturing conditions to support the growth of undifferentiated hES cells. Human ES cells were cultured under the following culturing conditions: Mouse embryonic fibroblasts (MEFs), bovine-fibronectin in the presence of TGFβ, LIF and bFGF (TLF BF), human-fibronectin in the presence of TGFβ, LIF and bFGF (TLF HF), bovine-fibronectin in the presence of TGFβ and bFGF (TF BF), human-fibronectin in the presence of TGFβ and bFGF (TF HF), bovine-fibronectin in the presence of LIF and TGFβ (LT), bovine-fibronectin in the presence of LIF and bFGF (LF), bovine-fibronectin in the presence of TGFβ alone (T) and bovine-fibronectin in the presence of bFGF alone (F). The percentages of undifferentiated cells were determined in two days increments.

FIGS. 9a-9f illustrate human ES cells and human ES cell colonies grown on feeder cells-free systems under various culture conditions. Shown are bright field images of the various ES cell lines grown on feeder cells-free systems. FIG. 9a—I-6 cell line grown on foreskin matrix in the presence of TLF for 5 passages (size bar represents 75 µM); FIG. 9b—I-3.2 cell line grown on Matrigel® for 12 passages in the presence of MEF conditioned medium (size bar represents 50 µM); FIG. 9c—I-6 cell line grown on MEF matrix in the presence of TLF for several passages (size bar represents 75 µM); FIG. 9d—I-3 cell line grown on fibronectin for 21 passages in the presence of TF (size bar represents 50 µM); FIG. 9e—I-6 cell line grown on Matrigel® for 12 passages in the presence of TLF (size bar represents 75 µM);

FIG. 9f—I-3 cell line grown on fibronectin in the presence of TF for 20 passages (size bar represents 38 µM); and FIGS. 10a-10f illustrate histological sections of teratomas in SCID-beige mice derived from the I-6 and I-3 ES cell lines grown on fibronectin (FIGS. 10a, and b), MEF matrix (FIGS. 10c, e and f) or Matrigel® (FIG. 10d). Teratoma sections, stained with Hematoxylin & Eosin, include gut-like epithelium including goblet cells (FIG. 10a), mature cartilage tissue (FIGS. 10b and c), embryonal myotubes (FIG. 10d), stratified epithelium (FIG. 10e) and myelinated nerve (FIG. 10f). Size bars represent 40 µM.

DESCRIPTION OF SPECIFIC EMBODIMENTS OF THE INVENTION

The present invention is of methods of establishing and propagating human embryonic stem cell lines employing feeder cells-free, xeno-free culture conditions. The present invention is further of human embryonic stem cell lines which are free of xeno-contaminants and are capable of being maintained in an undifferentiated, pluripotent and proliferative state in culture and thus are highly suitable for human therapy.

The principles and operation of the methods of preparing human embryonic stem cell line devoid of feeder and xeno contaminants according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

To maintain human ES cells in an undifferentiated state, ES cultures must provide the cells with conditions which maintain cell proliferation, inhibit ES cell differentiation and preserve pluripotency. Such culturing conditions are typically achieved by utilizing feeder cell layers which secrete factors needed for stem cell proliferation, while at the same time, inhibit their differentiation.

In order to traverse limitations associated with feeder cell layer use such as feeder cells contamination and undefined culture systems, more defined feeder cell-free culture systems have been developed. Feeder cell-free culture systems employ a matrix, which the ES cells are attached thereto, and a culture medium, which provides the ES cells with cytokines and growth factors needed for cell proliferation, while at the same time inhibits cell differentiation.

Commonly used matrices include the basement membrane preparation extracted from Engelbreth-Holm-Swarm (EHS) mouse sarcoma (e.g., Matrigel®) or bovine-fibronectin/laminin. Such matrices are usually supplemented with a mouse embryonic fibroblast (MEF) conditioned medium, or a synthetic medium supplemented with bovine serum and growth factors.

Previous attempts to culture human ES cells using feeder cells-free culture systems employed Matrigel® or laminin matrices supplemented with fresh culture medium and a growth factor mixture (U.S. Pat. Appl. No. 20030017589). However, these feeder cells-free matrices were derived from animal tissues and therefore may expose the human ES cells to animal pathogens. In addition, these experiments used a combination of six different growth factors at extremely high concentrations which may irreversibly damage the cultured cells. Indeed, as is demonstrated in U.S. Pat Appl. No. 20030017589, the doubling time of the ES cells was approximately 19 hours, suggesting a tumorigenic phenotype. Moreover, under these conditions only 50-70% of the cells exhibited an undifferentiated cell morphology following 14 passages on feeder cells-free culture systems.

Although such culturing conditions might be suitable for research purposes, human ES cells must be cultured under well-defined culture conditions which are essentially free of animal material when utilized for cell replacement therapy or tissue regeneration in humans.

While reducing the present invention to practice, the present inventors have devised feeder cell-free culturing conditions which are devoid of xeno-contaminants and yet are capable of sustaining human stem cells in culture for at least 38 passages. As is illustrated in the Examples section which follows, stem cell lines cultured under such conditions maintained all ES cell features including pluripotency, immortality, undifferentiated proliferation capacity and normal karyotype. Thus, the feeder cells-free culture system of the present invention provides, for the first time, a complete animal-free culturing environment, which is capable of maintaining human ES cells for at least 38 passages in a proliferative state while preserving ES pluripotency. In addition, more than 85% of ES cells cultured under such conditions exhibited undifferentiated cell morphology with a doubling time of 30-35 hours.

Thus, according to the present invention there is provided a method of establishing a human embryonic stem cell line capable of being maintained in an undifferentiated, pluripotent and proliferative state and being substantially free of xeno-contaminants.

As used herein, the phrase "stem cell line" refers to cells capable of differentiating into other cell types having a particular, specialized function (i.e., "fully differentiated" cells) or to cells capable of being maintained in an undifferentiated state, hereinafter "pluripotent stem cells".

Stem cells of the present invention can be hematopoietic stem cells obtained from bone marrow tissue of an individual at any age or from cord blood of a newborn individual, embryonic stem (ES) cells obtained from the embryonic tissue formed after gestation (e.g., blastocyst), or embryonic germ (EG) cells. Stem cell derivation and preparation is further described hereinbelow. Preferred stem cells of the present invention are human embryonic stem cells.

According to one aspect of the present invention, the method is effected by obtaining human embryonic stem cells and culturing the human embryonic stem cells under feeder cells-free culturing conditions which include a matrix and a tissue culture medium including growth factors to thereby establish a human embryonic stem cell line.

According to this aspect of the present invention, culturing is effected by plating the stem cells onto a matrix in a cell density which promotes cell survival and proliferation but limits differentiation. Typically, a plating density of between about 15,000 cells/cm$^2$ and about 200,000 cells/cm$^2$ is used.

It will be appreciated that although single-cell suspensions of stem cells are usually seeded, small clusters may also be used. To this end, enzymatic digestion utilized for cluster disruption (see Example 1 of the Examples section which follows) is terminated before stem cells become completely dispersed and the cells are triturated with a pipette such that clumps (i.e., 10-200 cells) are formed. However, measures are taken to avoid large clusters which cause cell differentiation.

The stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; Gardner et al., [Fertil. Steril. 69: 84, 1998].

It will be appreciated that commercially available stem cells can also be used with this aspect of the present invention. Human ES cells can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

Stem cells used by the present invention can be also derived from human embryonic germ (EG) cells. Human EG cells are prepared from the primordial germ cells obtained from human fetuses of about 8-11 weeks of gestation using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

As is mentioned hereinabove, the stem cells can are preferably cultured on a feeder cells-free culture system which includes a matrix instead of a feeder cell layer. As used herein, the term "matrix" refers to any matrix which can substitute the cell attachment function of feeder cells. Such a matrix typically contains extracellular components to which the stem cells can attach and thus it provides a suitable culture substrate.

Particularly suitable for use with the present invention are extracellular matrix components derived from basement membrane or extracellular matrix components that form part of adhesion molecule receptor-ligand couplings. Matrigel® is one example of a commercially available matrix (Becton Dickinson, USA) which is suitable for use with the present invention. Matrigel® is a soluble preparation from Engelbreth-Holm-Swarm tumor cells that gels at room temperature to form a reconstituted basement membrane; Matrigel® is also available as a growth factor reduced preparation. Other extracellular matrix components and component mixtures which are suitable for use with the present invention include laminin, fibronectin, proteoglycan, entactin, heparan sulfate, and the like, alone or in various combinations. Preferred matrices of the present invention are fibronectin derived matrices.

In cases where complete animal-free culturing conditions are desired, the matrix is preferably derived from a human source or synthesized using recombinant techniques. Such matrices include, for example, human-derived fibronectin recombinant fibronectin, human-derived laminin, foreskin fibroblast matrix or a synthetic fibronectin matrix. Human derived fibronectin can be from plasma fibronectin or cellular fibronectin, both of which can be obtained from Sigma, St. Louis, Mo., USA. Human derived laminin and foreskin fibroblast matrix can be obtained from Sigma, St. Louis, Mo., USA. A synthetic fibronectin matrix can be obtained from Sigma, St. Louis, Mo., USA.

Recombinant synthesis of matrix proteins can be effected by using expression vectors. The polynucleotide segments encoding the matrix protein (e.g., human plasma fibronectin) can be ligated into a commercially available expression vector system suitable for transforming mammalian cells such as HeLa cells and for directing the expression of this enzyme within the transformed cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides, etc.

Suitable mammalian expression vectors include, but are not limited to, pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Strategene, pTRES which is available from Clontech, and their derivatives.

According to preferred embodiments of the present invention, the culture medium includes cytokines and growth factors needed for cell proliferation [e.g., basic fibroblast growth factor (bFGF) and leukemia inhibitor factor (LIF)], and factors such as transforming growth factor $\beta_1$ (TGF$\beta_1$) which inhibit stem cell differentiation.

Such a culture medium can be a synthetic tissue culture medium such as Ko-DMEM (Gibco-Invitrogen Corporation products, Grand Island, N.Y., USA) supplemented with serum, serum replacement and/or growth factors.

Serum can be of any source including fetal bovine serum, goat serum or human serum. Preferably human serum or serum Replacement™ (Gibco-Invitrogen Corporation, Grand Island, N.Y. USA) are utilized in order to provide an animal-free environment for the human ES cells.

Serum Replacement™ includes albumin or albumin substitutes, amino acids, vitamins, transferrins or transferrin substitutes, antioxidants, insulin or insulin substitutes, collagen precursors and trace elements (International Patent Publication No. WO 98/30679 to Price, P. J. et al). To provide animal-free culture conditions the albumin or albumin substitutes are preferably derived from a human source and/or are recombinant proteins.

Culture medium, serum, and serum replacement can be obtained from any commercial supplier of tissue culture products, examples include Gibco-Invitrogen Corporation (Grand Island, N.Y. USA), Sigma (St. Louis Mo., USA) and the ATCC (Manassas, Va. USA).

The serum or serum replacement used by the present invention are provided at a concentration range of 1% to 40%, more preferably, 5% to 35%, most preferably, 10% to 30%.

According to presently preferred embodiments, the serum replacement is provided at a concentration of 15% (see Examples 1 and 4 of the Examples section).

Growth factors of the present invention can be used at any combination and can be provided to the stem cells at any concentration suitable for ES cell proliferation, while at the same time inhibit ES cell differentiation.

Suitable growth factors according to the present invention include, but are not limited to, transforming growth factor $\beta_1$ (TGF$\beta_1$), basic fibroblast growth factor (bFGF) and human recombinant leukemia inhibitor factor (LIF), ciliary neurotrophic factor (CNTF), recombinant human Oncostatin M, interleukin 6 (IL-6) Flt-3 ligand, stem cell factor (SCF) and the like. Such growth factors can be obtained from any supplier of tissue culture reagents such as Gibco Invitrogen Corporation Products, USA, R & D Systems Inc. Minneapolis, Minn., USA and Chemicon International Inc., Temecula, Calif., USA.

As shown in Example 1 of the Examples section which follows, when ES cells are cultured on bovine-fibronectin in the presence of culture medium supplemented with 20% serum replacement, both the TGF$\beta_1$ and bFGF (TF) combination of growth factors and the TGF$\beta_1$, LIF and bFGF (TLF) combination of growth factors are capable of maintaining human ES cells for at least 53 and 56 passages, respectively.

Thus, according to preferred embodiments of the present invention, the growth factors used to supplement the ES cells when cultured on a feeder cells-free system include TGF$\beta_1$, bFGF and/or LIF.

Under feeder cells-free culture systems, TGF$\beta_1$ is provided at a concentration range of 0.06-0.24 ng/ml, more preferably at 0.10-0.20 ng/ml, most preferably at 0.12 ng/ml, LIF is provided at a concentration range of 500-2000 u/ml, more preferably at 750-1500 u/ml, most preferably at 1000 u/ml, and bFGF is provided at a concentration range of 2-8 ng/ml, more preferably at 3-6 ng/ml, most preferably at 4 ng/ml.

Although less preferred, culturing hES cells can alternatively be effected using a conditioned medium instead of serum or serum replacement supplemented medium.

Conditioned medium is the growth medium of a monolayer cell culture (i.e., feeder cells) present following a certain culturing period. The conditioned medium includes growth factors and cytokines secreted by the monolayer cells in the culture.

Conditioned medium can be collected from a variety of cells forming monolayers in culture. Examples include MEF conditioned medium, foreskin conditioned medium, human embryonic fibroblasts conditioned medium, human fallopian epithelial cells conditioned medium, and the like.

Particularly suitable conditioned medium are those derived from human cells, such as foreskin-conditioned medium which is produced by culturing human foreskin cells in a growth medium under conditions suitable for producing the conditioned medium.

Such a growth medium can be any medium suitable for culturing feeder cells. The growth medium can be supplemented with nutritional factors, such as amino acids, (e.g., L-glutamine), anti-oxidants (e.g., beta-mercaptoethanol) and growth factors, which benefit stem cell growth in an undifferentiated state. Serum and serum replacements are added at effective concentration ranges as described elsewhere (U.S. patent application Ser. No. 10/368,045).

Feeder cells are cultured in the growth medium for sufficient time to allow adequate accumulation of secreted factors to support stem cell proliferation in an undifferentiated state. Typically, the medium is conditioned by culturing for 4-24 hours at 37° C. However, the culturing period can be scaled by assessing the effect of the conditioned medium on stem cell growth and differentiation.

Selection of culture apparatus for conditioning the medium is based on the scale and purpose of the conditioned medium. Large-scale production preferably involves the use of dedicated devices. Continuous cell culture systems are reviewed in Furey (2000) Genetic Eng. News 20:10.

Following accumulation of adequate factors in the medium, growth medium (i.e., conditioned medium) is separated from the feeder cells and collected. It will be appreciated that the feeder cells can be used repeatedly to condition further batches of medium over additional culture periods, provided that the cells retain their ability to condition the medium.

Preferably, the conditioned medium is sterilized (e.g., filtration using a 20 µM filter) prior to use. The conditioned medium of the present invention may be applied directly on stem cells or extracted to concentrate the effective factor such as by salt filtration. For future use, conditioned medium is preferably stored frozen at −80° C.

According to the method of the present invention, the stem cells are cultured under feeder cells-free culturing conditions to establish a human embryonic stem cell line.

An established human embryonic stem cell line is characterized by undifferentiated stem cells. According to the present invention an undifferentiated stem cell line comprises at least 50%, at least 60%, more preferably at least 70%, more preferably at least 80%, most preferably at least 85% of undifferentiated stem cells.

As described in Examples 1 and 4 of the Examples section which follows, undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described hereinbelow.

When cultured according to the teachings of the present invention, stem cell growth is monitored to determine their differentiation state. Several approaches, including, for example, morphological determination can be used to determine cellular differentiation of cells cultured as described herein.

According to preferred embodiments of the present invention the culturing conditions provide the stem cells with a complete xeno-free, feeder cells-free environment, capable of maintaining the stem cells in a proliferative, yet, undifferentiated state indefinitely. Thus, the culturing conditions include a human-derived (or recombinant) matrix and a culture medium supplemented with the $TGF\beta_1$, LW and bFGF growth factors.

As is shown in Examples 4 and 5 of the Examples section which follows, the present inventors have illustrated that ES cells can be cultured on human-derived fibronectin matrices, supplemented with human serum or serum replacement, thereby providing pluripotent stem cell cultures which are devoid of animal pathogens or any other contaminants. Under these conditions the ES cell line generated using the teachings of the present invention maintained a proliferative and undifferentiated state for at least 38 passages.

During the culturing step the stem cells are further monitored for their differentiation state. Cell differentiation can be determined upon examination of cell or tissue-specific markers which are known to be indicative of differentiation. For example, primate ES cells may express the stage-specific embryonic antigen (SSEA) 4, the tumour-rejecting antigen (TRA)-1-60 and TRA-1-81.

As is shown in Examples 2 and 4 of the Examples section which follows, ES cells grown on the feeder cells-free cultures supplemented with xeno-free culture medium and selected growth factors expressed the SSEA4, TRA-1-60 and TRA-1-81 cell surface markers typical for undifferentiated cells.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

Determination of ES cell differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, Calif., USA).

As is mentioned above, the stem cell line of the present invention maintains pluripotency for at least 38 passages. Such pluripotency can be monitored in vitro by the formation of embryoid bodies (EBs) as well as in vivo via the formation of teratomas.

Embryoid bodies are formed upon the removal of ES cells from feeder layers or feeder cells-free culture systems. ES cells removal can be effected using type IV Collagenase treatment for a limited time. Following dissociation from the culturing surface, the cells are transferred to tissue culture plates containing a culture medium supplemented with serum and amino acids. As is shown in Examples 3 and 5 of the Examples section which follows, following 14 days in a suspension culture, ES cells generated according to the teachings of the present invention differentiated into EBs which contained embryonic mesoderm, ectoderm and endoderm cells, thereby clearly demonstrating that the ES cell line of the present invention retains pluripotency under the feeder cells-free culture conditions used by the present invention.

The differentiation level of the EB cells can be monitored by following the loss of expression of Oct-4, and the increased expression level of other markers such as α-fetoprotein, NF-68 kDa, α-cardiac and albumin. Methods useful for monitoring the expression level of specific genes are well known in the art and include RT-PCR, RNA in situ hybridization, Western blot analysis and immunohistochemistry.

The pluripotent capacity of the ES cell line can also be confirmed by injecting cells into SCID mice [Evans M J and Kaufman M (1983). Pluripotential cells grown directly from normal mouse embryos. Cancer Surv. 2: 185-208], which upon injection form teratomas. Teratomas are fixed using 4% paraformaldehyde and histologically examined for the three germ layers (i.e., endoderm, mesoderm and ectoderm).

As is shown in Example 3 of the Examples section which follows, ES cells cultured on fibronectin-based feeder cells-free culture systems supplemented with the selected growth factor combinations of the present invention (i.e., the TF and the TLF combinations) formed functional teratomas, demonstrating the pluripotent capacity of the ES cells to differentiate in vivo.

In addition to monitoring a differentiation state, stem cells are often also being monitored for karyotype, in order to verify cytological euploidity, wherein all chromosomes are present and not detectably altered during culturing. Cultured stem cells can be karyotyped using a standard Giemsa staining and compared to published karyotypes of the corresponding species.

Stem cells cultured according to the teachings of the present invention retain a normal karyotype following 30 and 32 passages on fibronectin matrix when supplemented with the TF or the TLF combination of growth factors, respectively (see Example 2 of the Examples section).

Their pluripotency and ability to maintain a proliferative and undifferentiated state for at least 38 passages makes the ES cell cultures generated according to the teachings of the present invention an excellent source for single cell cloning.

Thus, the method described above can further include an additional step of culturing a single cell derived from the human embryonic stem cell line described above under the culturing conditions of the present invention which are preferably xeno-free and devoid of feeder cells to thereby establish a single cell derived ES culture.

Methods of single cell cloning are well known in the art (see for example U.S. Pat. No. 6,548,655, Amit et al., 2000, Dev. Biol. 227: 271-8). Such methods typically include selecting a group of cells from a cell culture, dissociating the group of cells into single cells and growing the single cells separately in conditions which promote cell proliferation, while at the same time, inhibit cell differentiation. Once obtained, single cell clones can be expanded into an ES cell line under suitable culturing conditions.

Since the ES cell line of the present invention is devoid of xeno and feeder contaminants it can be used for human cell-based therapy and tissue regeneration.

Thus, according to another aspect of the present invention there is provided a method of treating an individual in need of cell replacement and/or tissue regeneration, comprising administering hES stem cell preparation being free of xeno and feeder contaminants into the individual.

Preferably the method further comprises a step of preparing the hES cell preparation using the methodology described hereinabove.

As used herein "treating an individual in need of cell replacement and/or tissue regeneration" refers to treating an individual suffering from a disorder such as a neurological disorder, a muscular disorder, a cardiovascular disorder, an hematological disorder, a skin disorder, a liver disorder, and the like that require cell replacement and tissue regeneration.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "administering" refers to means for providing the human ES cell preparation to an individual, using any suitable route, e.g., oral, sublingual intravenous, subcutaneous, transcutaneous, intramuscular, intracutaneous, intrathecal, intra peritoneal, intra spleenic, intra hepatic, intra pancreatic, intra cardiac, epidural, intraoccular, intracranial, inhalation, rectal, vaginal, and the like administration.

The stem cells generated herein can be administered as is (i.e. an undifferentiated preparation) or following partial or complete differentiation. Cultured human ES cells can be differentiated into restricted developmental lineage cells, or terminally differentiated cells. Differentiation of stem cells can be initiated by allowing overgrowth of undifferentiated human ES cells in suspension culture forming embryoid bodies or by plating ES cells under conditions that promote differentiation in a particular manner. Such conditions may include withdrawing or adding nutrients, growth factors or cytokines to the medium, changing the oxygen pressure, or altering the substrate on the culture surface.

Undifferentiated or differentiated stem cells can be utilized in treating various disorders. For example, partially differentiated ES cells of the oligodendrocyte lineage can be used to treat myelin disorders (Repair of myelin disease: Strategies and progress in animal models. Molecular Medicine Today. 1997. pp. 554-561), partially differentiated ES cells of the chondrocytes or mesenchyme lineages can be used in treatment of bone and cartilage defects (U.S. Pat. No. 4,642,120) and partially differentiated ES cells of the epithelial lineage can be used in skin regeneration of a wound or burn (U.S. Pat. No. 5,716,411).

In addition to cell replacement therapy, the ES cell line of the present invention can also be utilized to prepare a cDNA library relatively uncontaminated with cDNA from feeder cells. mRNA is prepared by standard techniques from the ES cells and is further reverse transcribed to form cDNA. The cDNA preparation can be subtracted with nucleotides from embryonic fibroblasts and other cells of undesired specificity, to produce a subtracted cDNA library by techniques known in the art.

The ES cell line of the present invention can be used to screen for factors (such as small molecule drugs, peptides, polynucleotides, and the like) or conditions (such as culture conditions or manipulation) that affect the characteristics of stem cells. For example, growth affecting substances, toxins or potential differentiation factors can be tested by their addition to the culture medium.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); "Teratocarcinomas and Embryonic Stem Cells: A Practical Approach" Robertson E J, ed. (1987) Oxford: IRL Press; "Manipulating the Mouse Embryo" Nagy A et al., (2003) Cold Spring Harbor Lab Press, Third Edition; Thomson, J. A., Marshall, V. S. (1998) Primate embryonic stem cells. Current Topics in Developmental Biology 38, 133-165; Marshall, V. S., Waknitz, M. A., Thomson, J. A. (2001) Isolation and maintenance of primate embryonic stem cells. Methods in Molecular Biology 158, 11-18; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Feeder Cells-Free Culture Systems Supplemented with Xeno-Free Medium are Suitable for Growing ES Cell Lines Human ES cells were transferred to fibronectin-based culture systems in the presence of serum replacement and selected growth factors to provide a feeder cells-free, well-defined environment for ES cells cultures.

Materials and Experimental Methods

ES cell cultures—Human ES cell lines I-6, I-3 [Amit, M. & Itskovitz-Eldor, J. Derivation and spontaneous differentiation of human embryonic stem cells. J Anat. 200, 225-232 (2002)] and H-9 [Thomson, J. A., et al., Embryonic stem cell lines derived from human blastocysts. Science 282, 1145-7 (1998)] were cultured with mouse embryonic fibroblasts (MEF) for 46, 39 and 25 passages, respectively, in a culture medium consisting of 85% Ko-DMEM, supplemented with 15% serum replacement (SR), 2 mM L-glutamine, 0.1 mM β-mercaptoethanol, 1% non-essential amino acid stock, and 4 ng/ml bFGF (all from Gibco Invitrogen corporation products, USA). ES cells were then transferred to bovine-derived fibronectin-covered plates (50 μg/10 cm$^2$, Biological Industries, Beth Haemek, Israel) in the presence of 20% SR, 80% culture medium and one of the following combinations of growth factors: "T"—0.12 ng/ml TGFβ$_1$ (R&D Systems Inc. Minneapolis, Minn., USA); "TF"—0.12 ng/ml TGFβ$_1$ with 4 ng/ml bFGF (Gibco Invitrogen corporation products, USA); "LF"—1000 u/ml leukemia inhibitor factor (LIF, CHEMICON International, Inc., Temecula, Calif., USA) with 4 ng/ml bFGF; or "TLF"—0.12 ng/ml TGFβ$_1$, 1000 u/ml LIF and 4 ng/ml bFGF. Adherent cells were split every four to six days using 1 mg/ml Type IV Collagenase (Gibco Invitrogen corporation products, USA) for 30 min and re-plated in flasks containing fresh medium. According to the freezing protocol, cells were frozen in liquid nitrogen using freezing solution consisting of 10% DMSO (Sigma, St Louis, Mo., USA), 10% human serum (CHEMICON International, Inc., Temecula, Calif., USA) or 15% SR and 80% Ko-DMEM (Gibco-Invitrogen corporation products, USA).

Morphological Assessment—ES cells were examined under an inverted scope (live cells), using phase contrast (Olympus, IX70, Japan).

Experimental Results

Proliferation capacity of hES cells in feeder cells-free culture systems—ES cells from lines I-3, I-6 and H-9 were transferred to fibronectin-coated plates, in the presence of serum replacement supplemented with selected growth factors as detailed in Methods hereinabove. When the culture medium was supplemented with bFGF alone or with LIF and bFGF (LF), cells continued proliferation for several passages and then switched to differentiation. In addition, when ES culture medium was supplemented with TGFβ alone, ES cells remained at the undifferentiated stage for more than 10 passages but proliferated poorly and slowly faded away until passage 15. On the other hand, when ES culture medium was supplemented with TGFβ$_1$ and bFGF (TF) or with TGFβ1, LIF and bFGF (TLF) the cells continued to proliferate and maintained normal features of hES cells similarly to hES cells grown on MEF. However, while cells grown with the TF combination were split to a single plate during each passage, cells grown with the TLF combination were split to 2-3 plates, similarly to ES cells grown on MEF, demonstrating high proliferation rate in the presence of the TLF combination. Thus, the feeder cells-free culture system supplemented with the TLF combination of growth factors was able to support normal growth of hES cells, with a doubling time of at least 25 hours, similar to that of ES cells grown on MEF.

Morphological features of ES colonies and cells in feeder cells-free culture systems—The morphological features of ES colonies grown on the feeder cells-free culture system were indistinguishable from those of ES colonies grown on MEF, even after more than 56 passages (over 224 days) when supplemented with the TLF and 53 passages (more than 212 days) when supplemented with the TF combination of growth factors (not shown). In addition, at day four since their passage on the fibronectin feeder cells-free system of the present invention, hES cell cultures consisted of 85-90% of undifferentiated cells with a doubling time of 30-35 hours, which is consistent with the doubling time of hES cells were grown on MEF.

When viewed under higher magnification, hES cells grown on the feeder cells-free culture system were small and round with a high nucleus to cytoplasm ratio, a notable presence of one to three nucleoli and typical spacing between the cells (FIGS. 1a-d).

ES cells grown on a feeder cells-free culture system have a survival rate similar to that of ES cells grown on mef—For ES storage, ES cells grown on the feeder cells-free culture system were frozen in the presence of 15% SR and 10% DMSO. When frozen ES cells were further thawed and re-plated they exhibited a survival rate similar to that of ES cells grown on MEF.

Thus, these results demonstrate that the TF and the TLF combinations of growth factors are suitable for hES cultures with the TF combination inferior to the TLF combination due to low proliferation capacity. Furthermore, ES cells grown on the feeder cells-free culture system exhibited morphological features and survival rate similarly to that of ES cells grown on MEF.

Example 2

Feeder Cells-Free Culture Systems Supplemented with Xeno-Free Medium Support the Growth of Phenotypically Consistent ES Cells The phenotypic characteristics of hES cells grown on feeder cells-free culture systems supplemented with xeno-free medium were evaluated using cell surface markers typical of undifferentiated cells.

Materials and Experimental Methods

Karyotype analysis—ES cells metaphases were blocked using colcemid (KaryoMax colcemid solution, Invitrogen, Grand island, NY, USA) and nuclear membranes were lysed in an hypotonic solution according to standard protocols (International System for Human Cytogenetic Nomenclature, ISCN). G-banding of chromosomes was performed according to manufacturer's instructions (Giemsa, Merck). Karyotypes of at least 20 cells per sample were analyzed and reported according to the ISCN.

Immunohistochemistry—Cells were fixed for 20 min in 4% paraformaldehyde, blocked for 15 min in 2% normal goat serum in PBS (Biological Industries, Beth Haemek, Israel) and incubated for overnight at 4° C. with 1:50 dilutions of SSEA1, SSEA3, SSEA4 (Hybridoma bank, Iowa, USA), TRA-60, TRA-81 mouse anti-human antibodies, provided by Prof. P Andrews the University of Sheffield, England. Cells were then washed in PBS and further incubated with 1:100 dilutions of Donkey anti-mouse IgG antibodies conjugated to the fluorochrome Cys 3 (Chemicon International, Temecula Calif., USA). Cells were visualized under an inverted fluorescent microscope (CARL Zeiss, Germany) or a confocal microscope (Bio-Rad laboratories, Hertfordshire, England).

Experimental Results

Fibronectin-based feeder cells free culture systems supplemented with xeno-free culture medium provide ES cells with consistent karyotype as other feeder-based protocols—Karyotype analysis was performed on hES cells following continuous culturing on the fibronectin-based feeder cells-free culture systems supplemented with xeno-free culture medium. Karyotype analysis was carried out on nine separate cultures, representing the two medium conditions, TF and TLF, and the three hES cell lines (I-3, I-6 and H-9) at different stages from 6 to 32 passages on the feeder cells-free culture system. This analysis revealed normal karyotypes in 136 cells out of 140 cells examined at passage 30 when cultured on the TF medium and at passage 32 when cultured on the TLF medium. In four cells of the same group, an abnormal karyotype of 47, XXX was found. These four cells, cultured for almost one year, were at passage 71-post derivation of which 20 passages were on the feeder cells-free culture system supplemented with TLF. As is previously reported [Amit, M. et al. Clonally derived human embryonic stem cell lines maintain pluripotency and proliferative potential for prolonged periods of culture. Dev Biol 227: 271-8 (2000)], chromosomal instability may occur on ES cells when cultured for eight months on MEF. Taking together, these results suggest that the feeder cells-free culture systems of the present invention support normal and stable karyotype of hES cells.

Human ES cells cultured on feeder cells free culture systems supplemented with xeno-free medium express embryonic surface markers—In order to further characterize the ability of the fibronectin-based feeder cells-free culture systems to maintain normal growth of human ES cells, IHC was performed on human ES cells with embryonic surface marker antibodies including TRA-1-60, SSEA4, TRA-1-81, SSEA3 and SSEA1. Following 17 and 38 passages in cultures supplemented with the TF and TLF growth factors, respectively, the human I-3, I-6 ES cells demonstrated high expression levels of the stage-specific embryonic antigen 4 (SSEA4), the tumour rejecting antigen (TRA)-1-60, and TRA-1-81 (FIGS. 1e-h). These markers are typical characteristics of undifferentiated ES cells [Thomson J A, et al. (1998). Embryonic stem cell lines derived from human blastocysts. Science 282: 1145-7; Thomson J A, et al. (1996). Pluripotent cell lines derived from common marmoset (Callithrix jacchus) blastocysts. Biol Reprod 55: 254-9; Thomson J A, et al. (1995). Isolation of a primate embryonic stem cell line. Proc Natl Acad Sci USA 92: 7844-8]. Notably, the stage-specific embryonic antigen 3 (SSEA3) was only moderately expressed while expression of the stage-specific embryonic antigen 1 (SSEA1), a unique marker of mouse ES cells, was not detected (data not shown).

These results demonstrate that the feeder cells-free culture systems supplemented with TF or TLF growth factors are able to maintain human ES cells in an undifferentiated state even after prolonged culturing periods.

Example 3

Feeder Cells-Free Culture Systems Supplemented with Xeno-Free Medium Support the Growth of Functional ES Cells Human ES cells grown on the fibronectin-based feeder cells-free culture systems supplemented with serum replacement and xeno-free growth factors were tested for their capacity to form embryoid bodies in vitro and teratomas in vivo.

Material and Experimental Methods

Formation of embryoid bodies (EBs) from human ES cells—Human ES cells grown on the feeder cells-free culture systems were removed from the 6-well plate (40-60 $cm^2$) culture by Type IV Collagenase (1 mg/ml) and were further dissociated into small clamps using 1000 µl Gilson pipette tips. Thereafter, dissociated cells were cultured in 58 mm Petri dishes (Greiner, Germany) in a medium consisting of 80% Ko-DMEM, supplemented with 20% fetal bovine serum defined (FBSd, HyClone, Utah, USA), 1 mM L-glutamine, 0.1 mM β-mercaptoethanol, and 1% non-essential amino acid stock. Unless otherwise noted all were purchased from Gibco Invitrogen corporation, USA. Formation of EBs was examined following 14 days in suspension.

Teratomas formation—ES cells were drawn from 6 confluent wells in a six-well plate (60 cm²) and were injected into the rear leg muscle of 4-week-old male SCID-beige mice (Harlan, Jerusalem Israel). Resulting teratomas were fixed in formaldehyde and were examined histologically, at least 12 weeks post-injection.

Reverse transcriptase (RT) Coupled PCR—Total RNA was isolated from either undifferentiated human ES cells grown on the feeder cells-free culture systems for 17-25 passages or from 14 day-old EBs created from ES cells grown on feeder cells-free conditions using Tri-Reagent kit (Sigma-Aldrich Corp., St Louis, Mo., USA), according to the manufacturer's protocol. CDNA synthesis was performed on 1 μg total RNA template using MMLV RT-RNase H-minus (Promega Corp., Madison, Wis., USA) according to manufacturer's instructions. PCR primers and reaction conditions are described in Table 1, hereinbelow. All PCR reactions included an initial strand denaturation for 5 minutes at 94° C. PCR products were size-fractionated using 2% agarose gel electrophoresis.

TABLE 1

PCR primers and conditions

| Gene product (Accession number) | SEQ ID NOs. | Forward (F) and reverse (R) primers (5' Π 3') | Condition | Reaction | Size (bp) |
|---|---|---|---|---|---|
| Oct-4 (S81255) | SEQ ID NO: 1 SEQ ID NO: 2 | F: GAGAACAATG AGAACCTTCAGGA R: TTCTGGCGCC GGTTACAGAACCA | 30 cycles, annealing at 60° C., in 1.5 mM MgCl₂ | | 219 |
| Albumin (AF542069) | SEQ ID NO: 3 SEQ ID NO: 4 | F: TGCTTGAATGT GCTGATGACAGGG R: AAGGCAAGTCA GCAGCCATCTCAT | 35 cycles, annealing at 60° C., in 1.5 mM MgCl₂ | | 302 |
| α-feto-protein (BC027881) | SEQ ID NO: 5 SEQ ID NO: 6 | F: GCTGGATTGTC TGCAGGATGGGGAA R: TCCCCTGAAGA AAATTGGTTAAAAT | 30 cycles, annealing at 60° C., in 1.5 mM MgCl₂ | | 216 |
| NF-68KD (AY156690) | SEQ ID NO: 7 SEQ ID NO: 8 | F: GAGTGAAATGG CACGATACCTA R: TTTCCTCTCCT TCTTCACCTTC | 30 cycles, annealing at 60° C., in 2 mM MgCl₂ | | 473 |
| α-cardiac actin (NM 005159) | SEQ ID NO: 9 SEQ ID NO: 10 | F: GGAGTTATGG TGGGTATGGGTC R: AGTGGTGACA AAGGAGTAGCCA | 35 cycles, annealing at 65° C., in 2 mM MgCl₂ | | 486 |
| LIF-Receptor (NM 002310) | SEQ ID NO: 11 SEQ ID NO: 12 | F: CAAAAGAG TGTCTGTGAG R: CCATGTAT TTACATTGGC | 35 cycles, annealing at 61° C., in 1.5 mM MgCl₂ | | 459 |

TABLE 1-continued

PCR primers and conditions

| Gene product (Accession number) | SEQ ID NOs. | Forward (F) and reverse (R) primers (5' Π 3') | Condition | Reaction | Size (bp) |
|---|---|---|---|---|---|
| β-Actin (NM 001101) | SEQ ID NO: 13 SEQ ID NO: 14 | F: ATCTGGCAC CACACCTTCTAC AATGAGCTGCG R: CGTCATACT CCTGCTTGCTGA TCCACATCTGC | 35 cycles, annealing at 62° C., in 1.5 mM MgCl₂ | | 838 |

Experimental Results

ES cells spontaneously differentiate into embryonic germ layer cell types in vitro, following their removal from the feeder cells free culture systems—To verify that human ES cells cultured on fibronectin-based feeder cells-free culture systems are functionally, as well as phenotypically consistent with human ES cells derived by feeder-based protocols, the ES cells were removed from the feeder cells-free cultures following 22 to 30 passages in TLF and 28 passages in TF and were grown in suspension. As a result, hES cells formed embryoid bodies (EBs) similar to those created by ES cells grown on MEFs (FIGS. 2a-c). The functionality of the isolated EBs was further tested by IHC using various embryonic cell markers. As is further shown in FIGS. 2d-f, EBs expressed the neutral specific tubulin which is from an ectodermal origin, the smooth muscle actin and the CD-31 marker of mesodermal origin.

ES-consistent gene expression within the EBs was further verified using RT-PCR. Within the EBs stem cells differentiated into representative cells of the three embryonic germ layers i.e., mesoderm, endoderm and ectoderm. As shown in FIG. 3, while undifferentiated cells grown on feeder cells-free culture systems supplemented with TLF or TF expressed high levels of Oct 4 (FIG. 3), a marker for pluripotent embryonic stem and germ cells [Pesce M, and Scholer H R. Oct-4: gatekeeper in the beginnings of mammalian development (2001). Stem Cells 19: 271-8], cells harvested from 14-day-old EBs expressed genes, which are associated with cellular differentiation including neurofilament (NF-68 kD) which is related with embryonal ectoderm, α-cardiac actin which is associated with embryonal mesoderm, and α-fetoprotein and albumin both of which being indicators of embryonal endoderm. The diminished Oct 4 expression in EBs samples was consistent with previous reports of diminished Oct 4 expression following differentiation of totipotent cells to somatic lineages [Thomson J A, et al. (1998). Embryonic stem cell lines derived from human blastocysts. Science 282: 1145-7, Reubinoff B E, et al. (2000). Embryonic stem cell lines from human blastocysts: somatic differentiation in vitro. Nat. Biotechnol. 18: 399-404]. As have previously reported elsewhere [Schuldiner M. et al. Effect of eight-growth factors on the differentiation of cells derived from human ES cells. Proc Natl Acad Sci USA 97: 11307-12 (2000); Amit, M. et al., Human feeder layers for human embryonic stem cells. Biol. Reprod. 68: 2150-2156 (2003); Kehat, I. Et al. Human embryonic stem cells can differentiate into myocytes with structural and functional properties of cardiomyocytes. J Clin Invest 108: 407-14 (2001)] ES cell cultures might have some degree of background differentiation. Indeed, some of the cell-specific genes, like albumin and α-cardiac actin, were also expressed in the undifferentiated ES cells of the present invention (FIG. 3).

Thus, these results demonstrate that human ES cells grown on the feeder cells-free cultures of the present invention are capable of creating functional EBs with cells that are differentiated to the various somatic lineages.

Human ES cells cultured on feeder cells free cell cultures differentiate into embryonic germ layers in vivo—To further substantiate the ability of the feeder cells-free culture systems of the present invention to support the differentiation of human ES cells into embryonal germ layers, ES cells were tested for teratoma formation in vivo. Following injection to SCID Beige mice, the I-3 and I-6 cells cultured in TLF for 26 and 19 passages, respectively, were able to form teratomas. Each teratoma contained representative tissues of the three embryonic germ layers, including myelinated nerve of ectodermal origin (FIG. 4a), details of hyaline cartilage which is of mesodermal origin (FIG. 4b) and secretory epithelium rich in goblet cells which is related with an endoderm (FIG. 4c).

In conclusion, human ES cells grown on the feeder cells-free culture systems of the present invention were thus functionally indistinct from cells grown on feeder-based cultures. Following differentiation, ES cells expressed genes associated with all three embryonal germ layers, in vitro, and formed teratomas in vivo, consisting of tissue arising from all three germ layers, as well. Unlike other feeder cells-free protocols, the culture systems of the present invention contained a well-defined, xeno-free culture medium suitable for propagating human ES cells.

Example 4

Complete Xeno-Free, Feeder Cells-Free Culture Systems are Suitable for Growing Phenotypically Consistence Human ES Cells Since an animal-free environment is crucial for any future clinical use of human ES cells, a complete xeno-free, feeder cells-free culture system was developed using human-originated fibronectin as a matrix for culturing hES cells, and xeno-free supplemented medium and growth factors.

Experimental Results

Xeno-free, feeder cells free culture systems support the growth of human ES cells—To create a complete animal-free well-defined environment for hES cell cultures, human-originated fibronectin were used as feeder cells-free culture systems. The culture medium included serum replacement (15%) supplemented with the T, LF, TF and TLF growth factor combinations as described under Materials and Experimental Methods in Example 1 hereinabove. Both human plasma fibronectin (Fibronectin from human plasma, Sigma, St. Louis, Mo., USA) and cellular fibronectin (Fibronectin cellular from human foreskin fibroblast, Sigma, St. Louis, Mo., USA) were found to support the undifferentiated growth the hES cells for at least 38 passages (approximately 110 doublings) in the presence of both the TF and TLF growth factors combinations. In addition, on day four since passage on the fibronectin feeder cells-free system of the present invention, hES cell cultures consisted of 85-90% of undifferentiated cells with a doubling time of 30-35 hours, which is consistent with the doubling time of hES cells were grown on MEF, demonstrating the capacity of these xeno-free culture systems to propagate normal growth of hES cells.

These results demonstrate the capacity of human-originated fibronectin supplemented with xeno-free culture system to support the growth of long-lasting, proliferative and undifferentiated human ES cell cultures.

Human ES cells grown on xeno-free, feeder cells free culture systems are phenotypically indistinguishable from ES cells grown on bovine-derived fibronectin feeder cells free culture systems—Cells grown for 22 passages on human cellular fibronectin culture systems supplemented with serum replacement and the TF growth factors retained an undifferentiated cell morphology. ES cells were small and round, with a high nucleus to cytoplasm ratio, a notable presence of one to three nucleoli and typical spacing between the cells (FIGS. 5a-c).

In addition, human ES cells grown on a xeno-free, feeder cells-free culture system were found to have normal karyotype following 32 passages (not shown).

Moreover, as was further revealed by IHC, human ES cells cultured for 16 passages on a complete xeno-free, feeder cells-free system expressed all characteristic embryonic surface markers including TRA-1-60, SSEA4, TRA-1-81 (FIGS. 5d-f).

Thus, these results demonstrate the capacity of the complete xeno-free, feeder cells-free systems to support phenotypical consistence human ES cells, maintaining highly proliferative cultures with normal and stable karyotype and expressing all typical embryonic surface markers.

These results therefore suggest the use of the xeno-free, feeder cells-free culture systems of the present invention for derivation and culturing of human ES cells.

Example 5

Human ES Cell Grown on a Complete Xeno-Free, Feeder Cells-Free Culture Systems are Functionally Indistinguishable from ES Cells Grown on Other Culture Systems Human ES cells grown on human fibronectin-based feeder cells-free culture systems supplemented with serum replacement and xeno-free growth factors were tested for their capacity to form embryoid bodies in vitro.

ES cells spontaneously differentiate into embryonic germ layer cell types in vitro, following their removal from the feeder cells free culture systems—To verify that human ES cells cultured on a xeno-free, feeder cells-free culture systems are functionally, as well as phenotypically consistent with human ES cells derived by feeder-based protocols the ES cells were removed from the feeder cells-free cultures following 17 and 16 passages on the human cellular- and human plasma-fibronectin matrices, respectively. As a result, hES cells formed embryoid bodies (EBs) similar to those created by ES cells grown on MEFs (FIGS. 6a-c).

ES-consistent gene expression within the EBs was further verified using RT-PCR. Within the EBs stem cells differentiated into representative cells of the three embryonic germ layers i.e., mesoderm, endoderm and ectoderm. As shown in FIG. 7, while undifferentiated cells grown on xeno-free, feeder cells-free culture systems supplemented with TLF or TF expressed high levels of Oct 4 and LIF receptor (FIG. 7), cells harvested from 14-day-old EBs expressed genes, which are associated with cellular differentiation including neurofilament (NF-68 kD) which is related with embryonal ectoderm, α-cardiac actin which is associated with embryonal mesoderm, and α-fetoprotein and albumin both of which being indicators of embryonal endoderm.

Thus, these results demonstrate that human ES cells grown on the complete xeno-free, feeder cells-free cultures of the present invention are capable of creating functional EBs with cells that are differentiated to the various somatic lineages.

Example 6

Feeder Cells-Free Culture Systems Support Normal Growth Rates and High Percentages of Undifferentiated Human Embryonic Stem Cells To further characterize the capacity of the feeder cells-free culture systems to propagate human embryonic stem cells the growth rate and the fraction of undifferentiated stem cells were determined in hES cells under various culturing conditions.

Feeder cells free culture systems maintain normal growth rates and high percentages of undifferentiated human ES cells similar to feeder-based culture systems—To determine the capacity of the feeder cells-free culture systems of the present invention to support hES growth, the growth rate and the fraction of undifferentiated stem cells were determined in the feeder cells-free culture systems. As is shown in FIGS. 8a-c, when hES cells were cultured on a bovine-derived fibronectin matrix in the presence of the TLF combination of growth factors, the growth rates of the I-3 (FIG. 8a, pink curve), the I-6 (FIG. 8b, pink curve) and the H-9 (FIG. 8c, pink curve) hES cell lines were similar to that of hES cells cultured on MEFs. Moreover, when hES cells were cultured on a human-derived fibronectin matrix in the presence of only the TF combination of growth factors, the growth rates of the I-3 (FIG. 8a, light blue curve), the I-6 (FIG. 8b, light blue curve) and the H-9 (FIG. 8c, light blue curve) hES cell lines were similar to that of hES cells cultured on MEFs. On the other hand, when these cells were cultured on bovine-derived fibronectin matrix in the presence of the TF combination of growth factors the growth rates of the I-3 (FIG. 8a, black curve), the I-6 (FIG. 8b, black curve) and the H-9 (FIG. 8c, black curve) hES cell lines were lower as compared with hES cell lines cultured on MEFs. Thus, the bovine fibronectin matrix supplemented with the TLF combination of growth factors and the human fibronectin matrix supplemented with only the TF combination of growth factors support a high and normal growth rate of hES cells similar to that achieved on MEFs.

Human ES cells cultured on feeder cells free culture systems maintain high percentages of undifferentiated cells—To further characterize the capacity of the feeder cells-free systems of the present invention to propagate undifferentiated hES cell lines, the fractions of undifferentiated cells were determined following 4, 6 and 10 days in culture. As is shown in FIG. 8d, when hES cells were cultured on either human- or bovine-derived fibronectin matrices in the presence of the TF or the TLF combinations of growth factors a high percentage of the cells (85-90%) remained undifferentiated even following six days in culture. On the other hand, when hES cells were cultured on bovine-fibronectin matrix in the presence of the LT, LF, T or F combination of growth factors, the percentages of undifferentiated cells was 77-85% following 4 days in culture, and declined to 60-75% following 6 days in culture. Thus, these results demonstrate that the feeder cells-free culturing systems of the present invention utilizing fibronectin matrices and the TF or TLF growth factors are capable of maintaining a high fraction of undifferentiated cells, similar to that achieved under MEFs.

Example 7

The TLF and TF Combinations of Growth Factors are Suitable for Maintaining ES Cells on Other Feeder Cells-Free Culture Systems To further substantiate the capacity of the TLF and TF combinations of growth factors to supplement other feeder cells-free systems, additional matrices have been used.

Experimental Results

Human ES cells originally cultured on MEF were transferred to the following feeder cells-free culture systems: Matrigel®, home-made MEFs matrix and home-made foreskin fibroblast matrix, all been supplemented with serum replacement and selected combinations of growth factors. Using the TLF or the TF combinations of growth factors, hES cells were successfully grown on Matrigel®, MEFs matrix and foreskin fibroblast matrix (FIGS. 9a-f). When either Matrigel® or MEFs matrix were utilized, cells exceeded 30 passages at the undifferentiated stage (more than 120 days), created EBs and formed teratomas (FIGS. 10c-f). These matrices, however, are neither animal-free nor well-defined, leaving fibronectin the favourable option.

When ES cells were grown on foreskin fibroblast matrix supplemented with SR and the TF and TLF growth factors, the cells exceeded 5 passages at the undifferentiated stage (more than 20 days), preserving typical ES cell morphological features (FIG. 9a). Although this matrix represents an animal-free, feeder cells-free culture system, the foreskin fibroblast matrix is not a well-defined system as compared with the fibronectin matrix.

Thus, these results demonstrate that the xeno-free well-defined culture medium consisting of serum replacement and the TLF or TF combinations of growth factors are suitable for maintaining and propagating hES cells on a variety of feeder cells-free culture systems.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of maintaining a human pluripotent stem cell in an undifferentiated state, the method comprising culturing the human pluripotent stem cell in a serum-free culture medium under adherent conditions comprising culturing the human pluripotent stem cell on a matrix comprising basement membrane or extracellular matrix components, said culture medium comprising bFGF, TGFβ1 and at least one of transferrin and/or insulin, wherein said TGFβ$_1$ is provided at a concentration of at least 0.06 ng/ml, wherein said culture medium is capable of maintaining the stem cell in an undifferentiated state, thereby maintaining the stem cell in the undifferentiated state.

2. The method of claim 1, wherein said culture medium comprises bFGF, TGFβ1, transferrin and insulin.

3. The method of claim 1, wherein said culture medium is free of an animal contaminant.

4. The method of claim 1, wherein said culture medium is free of feeder cell contaminants.

5. The method of claim 1, wherein said bFGF is provided at a concentration of at least 2 ng/ml.

6. The method of claim 1, further comprising leukemia inhibitor factor (LIF).

7. The method of claim 6, wherein said LIF is provided at a concentration of at least 500 units/ml.

8. The method of claim 1, wherein said bFGF is provided at a concentration range of 2-8 ng/ml.

9. The method of claim 1, wherein said TGFβ1 is provided at a concentration range of 0.06-0.24 ng/ml.

10. The method of claim 1, wherein said TGFβ$_1$ is provided at a concentration range of 0.06-0.24 ng/ml, and said bFGF is provided at a concentration of at least 2 ng/ml.

11. The method of claim 6, wherein said LIF is provided at a concentration of 500-2000 units/ml.

12. The method of claim 6, wherein said TGFβ$_1$ is provided at a concentration range of 0.06-0.24 ng/ml, said bFGF is provided at a concentration of at least 2 ng/ml and said LIF is provided at a concentration of 500-2000 units/ml.

13. The method of claim 1, further comprising expanding the human pluripotent stem cell in an undifferentiated state for at least 5 passages in said medium.

14. The method of claim 1, wherein said matrix is selected from the group consisting of human plasma fibronectin matrix, recombinant human plasma fibronectin matrix, human cellular fibronectin matrix, recombinant human cellular fibronectin matrix, and synthetic fibronectin.

* * * * *